(12) United States Patent
Simanzhenkov et al.

(10) Patent No.: US 11,111,194 B2
(45) Date of Patent: Sep. 7, 2021

(54) ODH COMPLEX WITH ON-LINE MIXER UNIT AND FEED LINE CLEANING

(71) Applicant: NOVA Chemicals (International) S.A., Fribourg (CH)

(72) Inventors: Vasily Simanzhenkov, Calgary (CA); Shahin Goodarznia, Calgary (CA); Christina Orta, Calgary (CA); Kamal Serhal, Calgary (CA); Eric Clavelle, Calgary (CA); Michael Koselek, Red Deer (CA); Yoonhee Kim, Calgary (CA)

(73) Assignee: NOVA CHEMICALS (INTERNATIONAL) S.A., Fribourg (CH)

( * ) Notice: Subject to any disclaimer, the term of this patent is extended or adjusted under 35 U.S.C. 154(b) by 0 days.

(21) Appl. No.: 16/249,992

(22) Filed: Jan. 17, 2019

(65) Prior Publication Data
US 2019/0218161 A1  Jul. 18, 2019

(30) Foreign Application Priority Data
Jan. 18, 2018  (CA) .............................. CA 2992255

(51) Int. Cl.
*C07C 5/48* (2006.01)
*B01D 53/00* (2006.01)
(Continued)

(52) U.S. Cl.
CPC ................ *C07C 5/48* (2013.01); *B01D 5/003* (2013.01); *B01D 5/006* (2013.01); *B01D 53/002* (2013.01); *B01D 53/1475* (2013.01); *B01D 53/229* (2013.01); *B01D 53/26* (2013.01); *B01J 4/008* (2013.01); *B01J 8/0278* (2013.01);
(Continued)

(58) Field of Classification Search
CPC .............. B01D 53/002; B01D 53/1475; B01D 53/229; B01D 53/26; B01D 5/003; B01D 5/006; C07C 2523/32; C07C 2523/64; C07C 2523/755; C07C 5/48
See application file for complete search history.

(56) References Cited

U.S. PATENT DOCUMENTS 4,256,604 A   3/1981  Aida et al.
6,657,079 B1  12/2003 Mitsumoto et al.
(Continued)

FOREIGN PATENT DOCUMENTS

WO   2017/144584 A1   8/2017
WO   2018/007912 A2   1/2018

OTHER PUBLICATIONS

Peri, J.B. and Hensley, A.L., Jr.; The Surface Structure of Silica Gel; The Journal of Physical Chemistry; vol. 72, No. 8, Aug. 1968; pp. 2926-2933.
(Continued)

*Primary Examiner* — Sharon Pregler
(74) *Attorney, Agent, or Firm* — Fish & Richardson P.C.

(57) ABSTRACT

Oxidative dehydrogenation is an alternative to the energy extensive steam cracking process presently used for the production of olefins from paraffins. Various embodiments of an oxidative dehydrogenation chemical complex designed to allow removal of sulfur containing contaminants that collect in the gas mixer unit and in the feed lines leading to the ODH reactor are disclosed herein.

13 Claims, 4 Drawing Sheets

(51) Int. Cl.
*B01D 5/00* (2006.01)
*B01D 53/26* (2006.01)
*B01D 53/22* (2006.01)
*F25J 3/02* (2006.01)
*B01J 8/02* (2006.01)
*B01J 8/06* (2006.01)
*B01J 8/18* (2006.01)
*B01J 19/24* (2006.01)
*B01J 8/26* (2006.01)
*B01D 53/14* (2006.01)
*C10G 70/00* (2006.01)
*C10G 27/04* (2006.01)
*B01J 4/00* (2006.01)
*C10G 11/04* (2006.01)
*B08B 9/00* (2006.01)
*B08B 9/027* (2006.01)
*C11D 11/00* (2006.01)
*C10G 75/00* (2006.01)

(52) U.S. Cl.
CPC ............. *B01J 8/0285* (2013.01); *B01J 8/065* (2013.01); *B01J 8/067* (2013.01); *B01J 8/1827* (2013.01); *B01J 8/1836* (2013.01); *B01J 8/26* (2013.01); *B01J 19/2445* (2013.01); *B08B 9/00* (2013.01); *B08B 9/027* (2013.01); *C10G 11/04* (2013.01); *C10G 27/04* (2013.01); *C10G 70/00* (2013.01); *C10G 75/00* (2013.01); *C11D 11/0041* (2013.01); *F25J 3/0233* (2013.01); *B01J 2208/00115* (2013.01); *B01J 2208/00176* (2013.01); *B01J 2219/00038* (2013.01); *C07C 2523/32* (2013.01); *C07C 2523/64* (2013.01); *C07C 2523/755* (2013.01); *C10G 2300/4031* (2013.01); *C10G 2400/20* (2013.01); *F25J 2205/30* (2013.01); *F25J 2205/40* (2013.01); *F25J 2205/82* (2013.01); *F25J 2205/90* (2013.01); *F25J 2215/60* (2013.01)

(56) References Cited

U.S. PATENT DOCUMENTS

| | | |
|---|---|---|
| 7,414,149 B2 | 8/2008 | DeCourcy et al. |
| 8,404,189 B2 | 3/2013 | Andresen et al. |
| 8,500,894 B2 | 8/2013 | Andresen et al. |
| 9,545,610 B2 | 1/2017 | Simanzhenkov et al. |
| 10,343,957 B2 * | 7/2019 | Serhal .................... C07C 5/322 |
| 2004/0133057 A1 | 7/2004 | Jiang et al. |
| 2018/0009662 A1 * | 1/2018 | Simanzhenkov ......... B01F 3/02 |

OTHER PUBLICATIONS

PCT International Search Report and Written Opinion in International Application No. PCT/IB2019/050394, dated Apr. 16, 2019, 9 pages.
PCT International Preliminary Report on Patentability in International Application No. PCT/IB2019/050394, dated Jul. 21, 2020, 7 pages.

* cited by examiner

ODH COMPLEX WITH ON-LINE MIXER UNIT AND FEED LINE CLEANING

CROSS REFERENCE TO RELATED APPLICATIONS

This application claims the benefit of the earlier filing date of Canadian application serial number CA 2992255 filed on Jan. 18, 2018. The contents of Canadian application serial number CA 2992255 are incorporated herein by reference in their entirety.

TECHNICAL FIELD

The present disclosure relates generally to oxidative dehydrogenation (ODH) of lower alkanes into corresponding alkenes. More specifically, the present disclosure relates to a chemical complex for ODH that includes two upstream gas mixer units and a method for cleaning sulfur containing deposits from the gas mixers and feed lines to the ODH reactor.

BACKGROUND

Disclosed herein is a complex for oxidative dehydrogenation (ODH) of lower alkanes into corresponding alkenes. Various embodiments relate to a chemical complex for ODH that includes two gas mixer units associated with the ODH reactor and cleaning components and methods. Also disclosed are methods for operating the ODH reactor that allow for cleaning sulfur containing deposits from the gas mixing unit and/or from the feed lines from the mixer units into the reactor.

Catalytic oxidative dehydrogenation of alkanes into corresponding alkenes is an alternative to steam cracking, the method of choice for the majority of today's commercial scale producers. Despite its widespread use, steam cracking has its downsides. First, steam cracking is energy intensive, requiring temperatures in the range of 700° C. to 1000° C. to satisfy the highly endothermic nature of the cracking reactions. Second, the process is expensive owing to the high fuel demand, the requirement for reactor materials that can withstand the high temperatures, and the necessity for separation of unwanted by-products using downstream separation units. Third, the production of coke by-product requires periodic shutdown for cleaning and maintenance. Finally, for ethylene producers, the selectivity for ethylene is around 80-85% for a conversion rate that doesn't generally exceed 60%. In contrast, ODH operates at lower temperature, does not produce coke, and using newer developed catalysts provides selectivity for ethylene of around 98% at close to 60% conversion. The advantages of ODH are, however, overshadowed by the requirement for the potentially catastrophic mixing of oxygen with a hydrocarbon.

The concept of ODH has been known since at least the late 1960's. Disclosed herein are apparatus, tools, and processes for improved operation of the ODH complex.

SUMMARY

Provided herein is a chemical complex for oxidative dehydrogenation of lower alkanes, the chemical complex including in cooperative arrangement i) at least two mixers for premixing an oxygen containing gas and a lower alkane containing gas to produce a mixed feedstock stream and additionally including a cleaning loop; ii) at least one oxidative dehydrogenation reactor; wherein the at least two mixers are connected in parallel to the at least one oxidative dehydrogenation reactor so that either a first gas mixing unit or a second gas mixing unit is connected to the at least one oxidative dehydrogenation reactor during normal operations; and wherein an oxidative dehydrogenation catalyst contained within the at least one oxidative dehydrogenation reactor reacts with the mixed feed stock stream to produce a product stream including the corresponding alkene.

Also provided herein is a process for removing sulfur-containing deposits during the operation of an oxidative dehydrogenation reactor complex, the process including:
i) operating a chemical complex including in cooperative arrangement:
   a. at least two mixers for premixing an oxygen containing gas and a lower alkane containing gas to produce a mixed feedstock stream;
   b. at least one oxidative dehydrogenation reactor, wherein the at least two mixers are connected in parallel to the at least one oxidative dehydrogenation reactor so that either a first gas mixing unit or a second gas mixing unit is connected to the at least one oxidative dehydrogenation reactor during normal operations; and
wherein an oxidative dehydrogenation catalyst contained within the at least one oxidative dehydrogenation reactor reacts with the mixed feed stock stream to produce a product stream including the corresponding alkene;
ii) monitoring the pressure within the chemical complex during normal operation;
iii) switching from a first mixer for premixing the oxygen containing gas and the lower alkane containing gas to a second mixer when the a pressure drop is observed;
iv) purging the first mixer of the flammable hydrocarbons and oxygen by the means of gaseous of liquid purge;
v) introducing a cleaning solvent into the first mixer and cycling the cleaning solvent through a cleaning loop until the sulfur-containing deposits are removed;
vi) continuing to monitor the pressure within the complex during normal operation;
vii) switching back to the first mixer when a pressure drop is observed;
viii) introducing the cleaning solvent into the second mixer and cycling the cleaning solvent through a cleaning loop until the sulfur-containing deposits are removed; and
ix) repeating steps i)-viii) during continued operation of the chemical complex.

Also provided here in is a process for removing sulfur-containing deposits during the operation of an oxidative dehydrogenation reactor complex, the process including:
i) operating a chemical complex including in cooperative arrangement:
   a. at least two mixers for premixing an oxygen containing gas and a lower alkane containing gas to produce a mixed feedstock stream;
   b. at least one oxidative dehydrogenation reactor, and
   c. a feedline connecting each of the at least two mixers to the at least one oxidative dehydrogenation reactor, wherein the feedlines are fitted with sprayers to introduce a cleaning solvent to internal walls of the feedline.
wherein the at least two mixers are connected by the feedline in parallel to the at least one oxidative dehydrogenation reactor so that either a first gas mixing unit or a second gas mixing unit is connected to the at least one oxidative dehydrogenation reactor during normal operations; and wherein an oxidative dehydrogenation catalyst contained within the at least one oxidative dehydrogenation reactor reacts with the mixed feed stock stream to produce a product stream including the corresponding alkene;
   ii) monitoring the pressure within the chemical complex during normal operation;
   iii) introducing the cleaning solvent into the feedline through the sprayer to remove sulfur containing deposits when a pressure drop is observed in the chemical complex;
   iv) continuing to monitor the pressure within the chemical complex during operations and while the cleaning solvent is being introduced;
   v) stop the cleaning solvent flow once the pressure in the chemical complex returns to normal operating levels.

DETAILED DESCRIPTION

The present disclosure relates to oxidative dehydrogenation (ODH) of lower alkanes into corresponding alkenes. In some embodiments, there is a chemical complex useful for ODH and in another aspect there is described a process for ODH that may be performed in the chemical complex outlined in the first aspect. Lower alkanes are intended to include saturated hydrocarbons with from 2 to 6 carbons, and the corresponding alkene includes hydrocarbons with the same number of carbons, but with a single double carbon to carbon bond. For ethane, ethylene is its corresponding alkene.

In the following description disclosed herein for reference to the figures, it should be noted that like parts are designated by like reference numbers.

Gas Mixer

Figure 1:
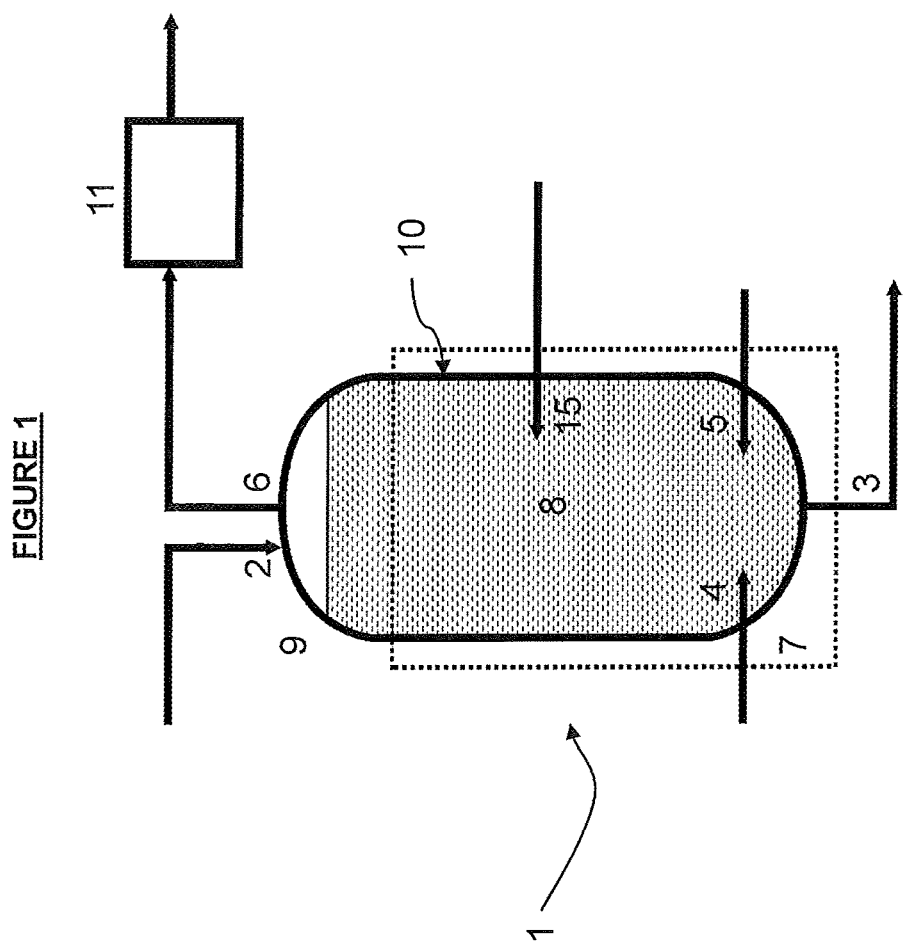
FIG. 1 is a schematic of a gas mixer.

A schematic representation of an embodiment of the gas mixer of the present disclosure is shown in FIG. 1. The gas mixer 1 includes a closed mixing vessel 10 having a top end 9 and a bottom end 7. The closed mixing vessel 10 is flooded with a non-flammable liquid, the choice of which depends on the application for which the mixed gas is to be used. Non-flammable liquid may be added to the closed mixing vessel 10 via a nozzle or inlet 2 located at the top end 9, while non-flammable liquid may be removed from the outlet 3 located at the bottom end 7.

Construction of the mixing vessel 10 can be accomplished with a variety of materials including stainless steel, carbon steel, and any other material chemically compatible with the hydrocarbon to be mixed. Furthermore, the lining of mixing vessel 10 may be coated with a spark suppressing material such as Teflon, sapphire, or oxide-based ceramic liners or the like.

Lower alkane containing gas may be introduced into the closed mixing vessel 10 through the lower alkane containing gas supply nozzle 4, while the oxygen containing gas may be introduced via oxygen containing gas supply nozzle 5. The lower alkane containing gas supply nozzle 4 and the oxygen containing gas supply nozzle 5 cooperate with the closed mixing vessel 10 in a way so that introduction of the gases directly into the non-flammable liquid occurs at or near the bottom end 7 of the closed mixing vessel 10. For the purposes of this disclosure, the term "nozzle" refers simply to the point where contact between the gases and the non-flammable liquid within the closed mixing vessel 10 first occurs, and can include any means known within the art. While not essential, the lower alkane containing gas supply nozzle 4 and the oxygen containing gas supply nozzle 5 may be orientated such that streams of the lower alkane containing gas and the oxygen containing gas impinge upon one another immediately upon entering the mixer. The introduced gases rise and are mixed through mixing zone 8 and are available for removal after exiting the non-flammable liquid at the top of the closed mixing vessel 10 through the mixed gas removal line 6. The mixed gas is optionally passed through a heat exchanger 11 and the optionally heated mixture then passes into a reactor, for example an ODH reactor.

As the term suggests, the non-flammable liquid used to flood the closed mixing vessel 10 is not flammable. That is, the non-flammable liquid is not capable of igniting or burning, for example, under conditions experienced within the reactor. Examples of suitable non-flammable liquids include water, ethylene glycol, silicon oils, and carbon tetrachloride. In some embodiments, water is used as the non-flammable liquid. While any non-flammable liquid may be used with the various embodiments disclosed herein, it is important to consider that mixed gas removed from the gas mixer 1 will include the lower alkane containing gas, oxygen containing gas, and in some instances carry over of non-flammable liquid. For this reason, selection of a non-flammable liquid also considers any potential effects the carry over may have on downstream applications. Catalysts used for oxidative reactions may be sensitive to catalytic poisoning by specific non-flammable liquids that are carried over in a gaseous state.

The temperature, along with the pressure, play a role in determining what fraction of the non-flammable liquid may enter the gaseous state, joining the hydrocarbon and oxygen gas present in bubbles that are mixing and rising to the top end of the closed mixing vessel 10. The temperature and pressure can be controlled to minimize the carryover of non-flammable liquid into the gas mixture leaving through mixed gas removal line 6. Temperature control using a heater, within or external the closed mixing vessel 10, is contemplated for use with the present disclosure. Heaters for use in mixing vessels similar to that of the present disclosure are well known. In some embodiments, the closed mixing vessel 10 is temperature controlled using a heater that is external to the closed mixing vessel 10. In another embodiment the closed mixing vessel 10 is temperature controlled using a heater that is located within the closed mixing vessel 10.

In some instances, it may be desirable for recycling purposes, to include a secondary lower alkane containing gas supply nozzle or product supply nozzle 15. For example, some oxidative reactions are not as efficient as others and may include conversion rates below an acceptable level. In those cases, it may be desirable to send a product line containing product and unreacted hydrocarbon back to start the oxidative reaction process again, with the intent of maximizing conversion of the starting hydrocarbon—the hydrocarbon originally mixed in the gas mixer before passage through an oxidative process. The product stream, similar to and containing unreacted starting hydrocarbon, would need to be mixed with oxidant before entering the reactor. If the product contained in the product stream is more reactive to oxygen than the starting hydrocarbon, it would be safer to introduce the product stream into the reactor at a point where the oxygen is already partially mixed and diluted. To this end, in some embodiments, the secondary lower alkane containing gas supply nozzle 15 is at a position distant from the oxygen containing gas supply nozzle 5. The position of the secondary lower alkane containing gas supply nozzle 15 is not critical, provided it is in a position where the oxygen present in the closed mixing vessel 10 has begun mixing with the lower alkane containing gas, and there is sufficient residence time for the product gas to mix thoroughly with the added oxygen and lower alkane containing gases. In some embodiments, the position of the secondary lower alkane containing gas supply nozzle is near a point equidistant from the oxygen containing gas supply nozzle 5 and the point where mixed gas removal line 6 leaves the top end 9 of the closed mixing vessel 10. The secondary lower alkane containing gas supply nozzle 15 may also be used as an additional input location for the introduction of the lower alkane containing gas. In some embodiments, there is a secondary lower alkane containing gas supply nozzle 15 for introducing a product stream from an oxidative process or additional lower alkane containing gas into the closed mixing vessel 10 at a point distant from oxygen containing gas supply nozzle 5.

In embodiments where there is recycling of an oxidative process such that a product line is fed back to the gas mixer 1 for introduction into the closed mixing vessel 10 via the secondary lower alkane containing gas supply nozzle 15, it is contemplated that heat from the product line may be used in temperature control of the closed mixing vessel 10. The heat provided from an oxidative process, for example ODH, may be used in this fashion and would therefore assist in reducing the cost associated with providing heat through an internal or external heater. In another embodiment, the closed mixing vessel 10 is temperature controlled using heat from a product line leaving an exothermic oxidation process.

Internal Mixing Means

The efficiency of mixing of the gases within zone 8 is dependent upon, among other things, the residence time and the frequency of interactions between bubbles of gas. In other words, how often do bubbles collide, break, and reform together, permitting mixing of the gas compositions from each of the bubbles which combine to form a homogeneous mixture. Means for promoting mixing are well known in the art and include use of a static mixers, random packing, structured packing, and impellers.

Static mixers promote mixing by creating a multitude of tortuous pathways that increase the distance that bubbles need to travel to reach the top of the vessel and consequently static mixers act partly by increasing the residence time. Also, the pathways include limited space that results in an increased probability that bubbles collide and ultimately mix to combine their gaseous contents. In some embodiments, the internal mixing means includes a static mixer.

Random and structured packing act similar to static mixers in that they provide for increased residence time and probability of interaction between bubbles by creation of a plethora of winding pathways. Random packing involves filling at least a part of the closed mixing vessel with a packing material that includes objects of varying shape and size that create random pathways for the bubbles to follow as they rise to the top. An example of commonly used random packing is glass beads of varying diameter. In some embodiments, the internal mixing means includes a packed bed.

Structured packing also increases residence time and probability of contact between bubbles, but differs from random packing in that the structured packing has an ordered arrangement so that most of the pathways are of a similar shape and size. Random and structured packing are supported within the gas mixer using means known in the art. In some embodiments, the internal mixing means includes structured packing.

The present disclosure also contemplates the use of power driven mixers, which can promote interactions by creating flow within the vessel. Impellers include a rotating component, driven by a motor that may force the non-flammable liquid, and associated bubbles of gas, to the outside wall and away from the center of rotation. Impellers can create axial flow or radial flow depending upon design, and can be further sub-typed as propellers, paddles, or turbines. Furthermore, the position of the impeller may be subject to change through vertical movement throughout the mixing zone. Motor driven pumping of an impeller further improves mixing. In some embodiments, the closed mixing vessel includes an impeller.

Similar to the closed mixing vessel, the internal mixing means, whether a static mixer, random or structured packing, or an impeller may be comprised of any material that is chemically compatible with the hydrocarbon to be mixed.

The shape and design of the closed mixing vessel impacts the residence time. The overall shape of the vessel is not critical, but the distance between where the gas enters and exits the mixing zone should be considered when designing the unit. The point of first contact between the gases and the water in the closed mixing vessel should be a distance from the top that allows for a residence time that permits complete mixing before removal. In some embodiments, the entry point is near the bottom of the vessel. Where the lines containing the gas enter the vessel is not important, provided the nozzle—the point where the gas contacts the water in the vessel—is in the position where residence time is sufficient.

Another consideration for the optimum mixing of the gases is the surface area over which the gases are dispersed. A larger surface area of dispersion promotes better mixing. While injection through a single inlet is feasible, provided sufficient residence time, more thorough mixing occurs when a larger number of smaller bubbles are dispersed over a larger surface area. Having multiple lower alkane containing gas supply nozzles and multiple oxygen containing gas supply nozzles allows each of the gases to be introduced in multiple locations. Conversely, a single nozzle may include multiple exit points where gas can enter the vessel, effectively dispersing the gas over a greater surface area compared to dispersion from a nozzle with a single exit point. In some embodiments, at least one of the lower alkane containing gas supply nozzle 4 and the oxygen containing gas supply nozzle 5 includes a sparger.

In some embodiments, the lower alkane containing gas supply nozzle 4 and the oxygen containing gas supply nozzle 5 are arranged as spargers in the form of concentric rings. Furthermore, the exit points for the lower alkane containing gas and the oxygen containing gas from their respective nozzles are arranged such that the streams of gas impinge on one another, initiating mixing as early as possible after introduction into the mixer. The arrangement of the gas supply nozzles is not limited to examples provided here. As another example, a series of concentric rings, with alternating oxygen and lower alkane containing gas supply nozzles, is also contemplated.

Emergency Shutdown

Another embodiment relates to emergency shutdown procedures common to oxidative reaction processes. It is well known that when undesirable conditions occur in an oxidative reaction process an emergency shutdown procedure can be initiated to limit damage to equipment, reduce likelihood of personal injury, and prevent or minimize release of chemicals into the surrounding environment. Known emergency shutdown procedures include the cessation of adding reactants while at the same time providing a flow of an inert material, such as nitrogen, to the reaction zone to displace the reactants from the reactor.

In some embodiments, it is contemplated that for an additional safety component an inert material inlet, located near the top end and above the liquid level, may be included for the introduction of a flow of an inert material. In addition, a suppression outlet leading to any known explosion suppression system may be included near the top end of the gas mixer. When an unsafe operating condition is detected at any point in the oxidative process, flow of an inert material through the inert material inlet can be initiated while the suppression outlet can be opened. These events can be coordinated with a reduction or termination of the hydrocarbon and oxidant reactants. The end result is that any mixed gases within the mixer are displaced to the explosion suppression system or to downstream components of the oxidative process. The flow of inert material acts as diluent and promotes movement in a single direction so that backflow of materials from the oxidation reactor into the gas mixer are prevented, In some embodiments, the gas mixer further includes an inert material inlet, located near the top end of the gas mixer, for introducing an inert material into the gas mixer above the level of the non-flammable liquid, and a suppression outlet for removing gaseous mixtures, located near the top end of the gas mixer and leading to an explosion suppression system.

Method for Mixing a Lower Alkane Containing Gas and a Oxygen Containing Gas

The present disclosure is relevant for applications that include the mixing of a lower alkane containing gas with an oxygen containing gas. It is well known that gaseous compositions containing a hydrocarbon and oxygen in ratios that fall within the flammability envelope are potentially hazardous. An ignition event, such as a spark, can ignite the mixture and potentially lead to an explosion. While applications that require mixing of hydrocarbons and oxygen normally do so with ratios that are safe and not susceptible to ignition there are moments during initial mixing where heterogeneous pockets of unfavorable hydrogen/oxygen compositions exist and may ignite if a spark occurs.

The present disclosure seeks to provide a method for mixing a lower alkane containing gas with an oxygen containing gas that is simple, and safe in that ignition events are unlikely to occur. The method includes introducing, separately and simultaneously, a lower alkane containing gas and an oxygen containing gas directly into a closed mixing vessel having a top end and a bottom end and flooded with a non-flammable liquid, in close proximity (e.g., within 15% or 10% of the length of the reactor) to the bottom end, allowing the bubbles of gas to mix while surrounded by the non-flammable liquid, and removing from the top of the vessel, after mixing is complete, a homogeneous mixture of the lower alkane containing gas and the oxygen containing gas in a ratio that is outside of the flammability envelope.

In some embodiments, the amount of the gases introduced into the bottom end of the closed mixing vessel 10 will result in a final composition that includes a ratio of lower alkane containing gas to oxygen containing gas that is outside of the flammability envelope. The chosen ratio will depend on the nature of the gases and the application for which the mixture will be used. For example, for an ODH application, the ratio of ethane to oxygen chosen will depend on whether under the proposed ODH reaction conditions the ratio is above the higher explosive limit or below the lower explosive limit. In comparison, the ratio of ethylene to oxygen added to the reactor would be different because ethylene is more reactive than ethane. The temperature of the ODH process to be employed should also be taken into consideration as higher temperatures correspond to a much smaller window of safe ratios of ethane to oxygen. For example, a molar ratio of about 80:20 ethane to oxygen for catalytic ODH would fall above the upper explosive limit, while a ratio of about 1.5:98.5 ethane to oxygen would fall below the lower explosive limit, with each ratio safe enough in that ignition events would not lead to an explosion or flame propagation under ODH reaction conditions. Ratios falling between that—50:50 for example—would be unsafe and potentially flammable/explosive.

The next consideration after determining the desired final ratio of hydrocarbon to oxygen is determining the flow rate at which each gas is added to the bottom of the closed mixing vessel 10. The flow rate of the gases and the corresponding pressure would need to be higher than the pressure of the non-flammable liquid in the closed mixing vessel 10. In the absence of a pressure differential, the gases cannot enter the closed mixing vessel 10 and consequently the mixing zone 8. Furthermore, if the pressure of the non-flammable liquid is higher than the line containing the gas to be introduced there may be, in the absence of a one-way valve, flow back of non-flammable liquid into the gas supply lines. This should be avoided.

When determining flow rates, the skilled worker correlates the flow rates with the pressure and temperature used within the closed mixing vessel 10. The conditions within the closed mixing vessel 10 are chosen to reflect the amount of carryover of non-flammable liquid into the gas mixture removed through mixed gas removal outlet 6. In some embodiments, flow rates of the incoming gases allow entry into the non-flammable liquid at the predetermined temperature and pressure.

As a further safety precaution, the present disclosure also contemplates embodiments where the dilution of the oxygen containing gas with non-flammable liquid prior occurs to entry into the closed mixing vessel 10. The prior dilution of the oxygen containing gas permits the saturation of incoming oxygen molecules with molecules of the non-flammable liquid that discourage ignition events igniting any hydrocarbons that interact with the oxygen during the early stages of mixing. Dilution of the oxygen containing gas with non-flammable liquid can be accomplished by directing a non-flammable liquid line into the oxygen containing gas line prior to the oxygen containing gas nozzle. Non-flammable liquid present within the closed mixing vessel 10 that is ejected via outlet 3 may be suitable for this purpose, provided this non-flammable liquid passes through a filter to remove particulate matter prior to introduction into the oxygen containing gas line. In some embodiments, the oxygen containing gas is diluted with non-flammable liquid prior to introduction into the closed mixing vessel 10.

The choice of gas mixer and associated design of the closed mixing vessel should consider the factors discussed above. In some embodiments, gas mixers allow for a residence time that allows complete, or near complete, mixing to create a homogeneous composition of gas where there are no potentially unsafe pockets of gas with undesirable ratios of hydrocarbon to oxygen.

The final consideration is the removal of the mixed gas from the top of the closed mixing vessel, which can be accomplished with any variety of means for removal well known in the art.

Twinned $O_2$/HC Mixer Tower

Figure 2:
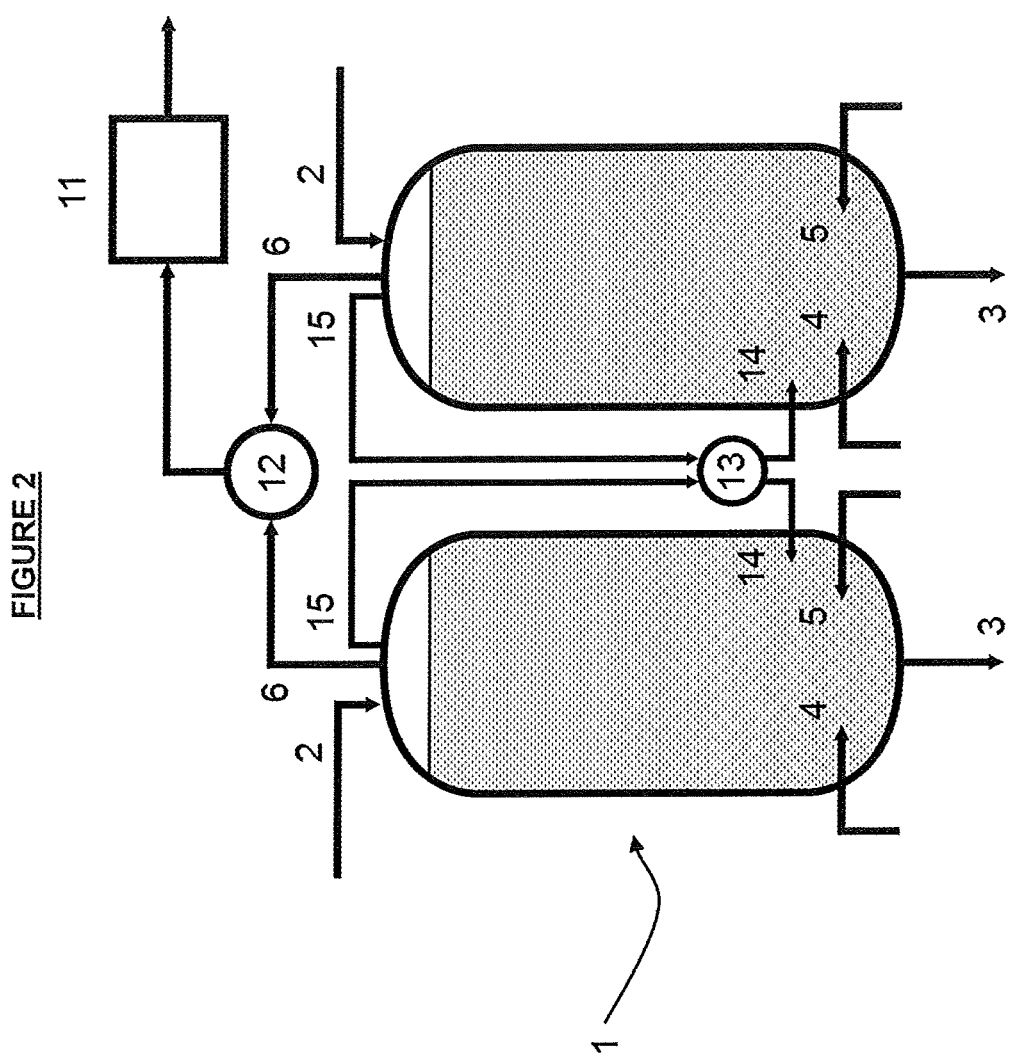
FIG. 2 is a schematic of a twined gas mixer unit.

In some embodiments, of the present disclosure at least two gas mixer units are associated with and integrated into the complex including the ODH reactor. An example of a twinned mixer is shown in FIG. 2. In these embodiments, the mixed gas from either of the mixer units 1 can be introduced to the ODH reactor after exiting the top of the closed mixing vessel through the mixed gas removal line 6. A valve configuration 12 allows for either switching between the two gas mixer units or allowing both gas mixer units to feed into the reactor (after passing through the optional heat exchanger 11) at the same time.

Sulfur Containing Deposits

Another aspect of the present disclosure focuses on the ability to remove sulfur and sulfur containing deposits that are created as a result of mixing the feed gases. A very common contaminant in ethane feeds to petrochemical plants is $H_2S$ and in some cases elemental sulfur (refinery paraffin/olefin sources). It is known that when $H_2S$ is combined with oxygen at low temperatures one result may be formation of deposits including elemental sulfur or solid sulfur-rich compounds. In a reactor environment this can lead to severe equipment fouling and potential shutdown of the equipment. Considering the tight specifications typically in place for $H_2S$ concentration in feed streams, the rate of fouling is usually rather low, yet it is nonetheless very likely to occur and to build up over time. In some instances, pretreatment steps are put in place to remove any $H_2S$ prior to exposure of the feed streams to oxygen, however, even the best of technologies may result in breakthrough of $H_2S$ to downstream equipment. As such methods to address the removal of those deposits are useful in, for example, ODH reactor complexes.

There are known methods to remove sulfur based fouling, and/or coke deposits from reactors. Disclosed herein however, are methods for removal of deposits in premixers as well as the feed lines that lead from the mixer unit into a reactor. These methods are not specifically intended to address deposits within a reactor. The methods disclosed use a combination of a twinned $O_2$/HC mixer tower as detailed herein above and shown in FIG. 2, or any other kind of mixer unit, wherein the mixer unit includes injection ports prior to the inlet of the reactor to introduce a solvent that would have little or no impact on the ODH reactor section performance but would dissolve and/or remove the fouling deposits.

A cleaning solvent is any solvent that dissolves or loosens or dislodges or suspends in the cleaning solvent, the sulfur containing deposits and does not affect the operation of the ODH reactor. One such compound, which has been demonstrated to dissolve elemental sulfur as well as sulfur-rich organic fouling compounds is dimethyl disulfide (DMDS). This solvent also meets the requirement of allowing the ODH catalyst and ODH process to proceed as desired when used to remove deposits while the reactor remains in operation. It is speculated that DMDS is a good material to dissolve solid sulfur fouling as it does not act as a true solvent, but rather as a reactant. The sulfur-rich organic fouling enters an equilibrium with the DMDS solvent which allows it to remain in the liquid phase regardless of temperature. It is stated in the literature that DMDS is capable of taking up as much as 600 weight percent (wt. %) of elemental sulfur as polysulfides at 80° C. Other potentially useful solvents or reactants for dissolving sulfur-rich organic fouling compounds include carbon disulfide and warm or hot toluene. In some embodiments, the toluene is warmed to temperatures below the boiling point. In some embodiments, the toluene is heated to about 80° C.

Determining when the mixer units or feed lines have sulfur-rich organic fouling that requires cleaning is something that is known to a person of ordinary skill in the art and can be done by monitoring the pressure within the complex at various points in the system. When there is a pressure difference at two different measured points, that indicates that fouling has occurred and cleaning may be needed. In other embodiments, the amount of $H_2S$ or total sulfur on the inlet to the mixer, on the outlet of the mixer, and inlet to the reactor, can be monitored. The measured values can be used to indicate the size the fouling in the corresponding section of the equipment.

An example of a chemical complex for oxidative dehydrogenation of lower alkanes includes in cooperative arrangement: i) at least two mixers for premixing an oxygen containing gas and a lower alkane containing gas to produce a mixed feedstock stream and additionally including a cleaning loop; and ii) at least one oxidative dehydrogenation reactor. In some embodiments, the at least two mixers are connected in parallel to the at least one oxidative dehydrogenation reactor so that either a first gas mixing unit or a second gas mixing unit is operating and connected to the at least one oxidative dehydrogenation reactor during normal operations. In some embodiments, the at least two mixers are connected in parallel to the at least one oxidative dehydrogenation reactor so that both the first gas mixing unit and the second gas mixing unit are operating and connected to the at least one oxidative dehydrogenation reactor during normal operations. The oxidative dehydrogenation catalyst contained within the at least one oxidative dehydrogenation reactor reacts with the mixed feed stock stream to produce a product stream including the corresponding alkene.

While it is most likely that the complex will be operated using a single mixer unit which is alternated with the other mixing unit once fouling is detected, it is also contemplated that the complex can be operated while both mixer units are online. Both mixers can be shut down and cleaned, but the presently disclosed apparatus and methods allows for the advantage of cleaning the mixer units while the complex continues to operate. In some embodiments, when fouling is detected a single unit can be isolated and cleaned while the other continues operating.

The cleaning loop is an arrangement of inlets and outlets on the mixer unit that provide for the i) injection of cleaning solvents into the mixer unit ii) circulation of solvent in the mixer unit, iii) removal of cleaning solvent from the mixer unit. The cleaning loop inlets may be located at any position in the mixer unit(s) that allows for cleaning. In some embodiments, the cleaning loop inlets may be at or near the lower alkane containing gas supply nozzle or at or near the oxygen containing gas supply nozzle (14 in FIG. 2). In other embodiments, the cleaning loop inlets may be at or near the mixed gas removal line. In some embodiments, the cleaning loop outlets are located at or near the mixed gas removal line (15 in FIG. 2). In other embodiments, the cleaning loop outlets may be at or near the lower alkane containing gas supply nozzle or at or near the oxygen containing gas supply nozzle.

In some embodiments, the cleaning loop further includes a pump 13, and/or a filter, and/or a small heating vessel. In some embodiments, the solvent is heated to about 60° C., or for example to about 80° C. degrees during the cleaning process. The temperature should be kept below the boiling point of the solvent used for cleaning (e.g., the oiling point of DMDS is 110° C.).

In some embodiments, the complex further includes a knock-out vessel, after the mixed feedstock stream outlet and in close proximity (e.g. within about the length of the dehydrogenation reactor) to the at least one oxidative dehydrogenation reactor, wherein the knock-out vessel is configured to receive condensed cleaning solvent. The condensed cleaning solvent may also contain the dissolved sulfur fouling material.

In some embodiments, either in addition to or instead of the cleaning loop, the complex further includes sprayers that are fitted on to the feedlines between the mixer units and the at least one oxidative dehydrogenation reactor, which allows the solvent to be sprayed onto the internal walls of the feedline.

Figure 3:
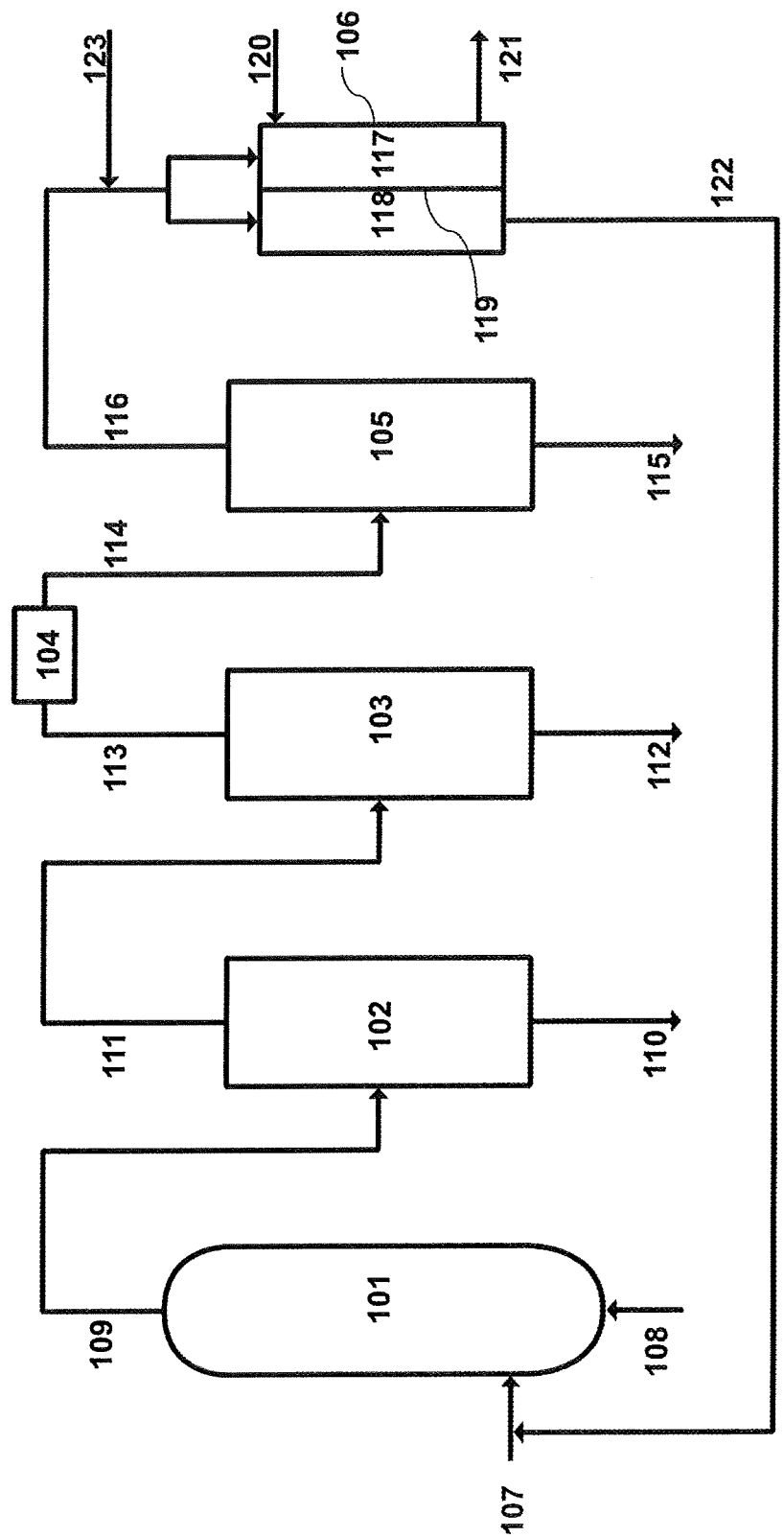
FIG. 3 is a schematic of a chemical complex that can benefit from the cleaning apparatus and methods disclosed herein.

The feedlines are any of the pipes or feeds between the mixer unit 10, the optional heat exchange unit 11, and the reactor 101, shown but not numbered in FIGS. 1, 2, and 3.

The sprayer, also commonly referred to as an atomizer, can take numerous forms depending on the cleaning solvent properties, receiving fluid (e.g., mixed feed stock) properties and flow rates and the local geometry (e.g., pipe diameter, pipe length, bends or elbows). The sprayer can be flush to the pipe wall or inserted on a small pipe or lance to position it in an optimal way to maximize coverage of the walls by the spray. The sprayer typically will have the cleaning solvent supplied to it at a pressure significantly higher than the pressure in the feed stock piping. This pressure is used with the geometry of the sprayer nozzle to atomize the solvent into droplets that will coat the walls of the receiving pipe. The sprayer nozzle may have multiple holes, use swirl or, in some embodiments, use a high pressure gas to obtain the required solvent droplet size and droplet spray pattern to cover the internal walls of the feedline. SPRAYING SYSTEMS CO.® is a company that sells numerous spray nozzles designs and spray nozzle holders (also referred to as quills, lances, or injectors).

In some embodiments, the process for removing sulfur-containing deposits during the operation of an oxidative dehydrogenation reactor complex includes
  i) operating a chemical complex including in cooperative arrangement:
    a. at least two mixers for premixing an oxygen containing gas and a lower alkane containing gas to produce a mixed feedstock stream; and
    b. at least one oxidative dehydrogenation reactor,
  wherein the at least two mixers are connected in parallel to the at least one oxidative dehydrogenation reactor so that either a first gas mixing unit or a second gas mixing unit is connected to the at least one oxidative dehydrogenation reactor during normal operations; and
  wherein an oxidative dehydrogenation catalyst contained within the at least one oxidative dehydrogenation reactor reacts with the mixed feed stock stream to produce a product stream including the corresponding alkene;
  ii) monitoring the pressure within the chemical complex during normal operation;
  iii) switching from a first mixer for premixing the oxygen containing gas and the lower alkane containing gas to a second mixer when a pressure drop is observed;
  iv) purging the first mixer of the flammable hydrocarbons and oxygen by the means of gaseous or liquid purge;
  v) introducing cleaning solvent into the first mixer and cycling cleaning solvent through a cleaning loop until the sulfur-containing deposits are removed;
  vi) continuing to monitor the pressure within the complex during normal operation;
  vii) switching back to the first mixer when a pressure drop is observed;
  viii) introducing cleaning solvent into the second mixer and cycling cleaning solvent through a cleaning loop until the sulfur-containing deposits are removed; and
  ix) repeating steps i)-viii) during continued operation of the chemical complex.

In some embodiments, the process for removing sulfur-containing deposits during the operation of an oxidative dehydrogenation reactor complex includes
  i) operating a chemical complex including in cooperative arrangement:
    a. at least two mixers for premixing an oxygen containing gas and a lower alkane containing gas to produce a mixed feedstock stream; and
    b. at least one oxidative dehydrogenation reactor,
  wherein the at least two mixers are connected in parallel to the at least one oxidative dehydrogenation reactor and both a first gas mixing unit and a second gas mixing unit are connected to the at least one oxidative dehydrogenation reactor during normal operations; and
  wherein an oxidative dehydrogenation catalyst contained within the at least one oxidative dehydrogenation reactor reacts with the mixed feed stock stream to produce a product stream including the corresponding alkene;
  ii) monitoring the pressure within the chemical complex during normal operation;
  iii) when a pressure drop is observed isolating at least one of the at least two mixers;
  iv) purging the mixer isolated in iii) of the flammable hydrocarbons and oxygen by the means of gaseous of liquid purge;
  v) introducing cleaning solvent into the isolated mixer from the previous step and cycling cleaning solvent through a cleaning loop until the sulfur-containing deposits are removed;
  vi) optionally repeating steps iv) and v) for the mixer unit that remained on line;
  vii) optionally returning to operation where the at least two mixers are operational.

In some embodiments, prior to introducing the cleaning solvent the mixer is drained, then flushed and dried with an inert gas. In some embodiments, the mixer is drained, then flushed and dried with an inert gas prior to being brought back online for normal operations.

In some embodiments, the process for removing sulfur-containing deposits during the operation of an oxidative dehydrogenation reactor complex includes:
  i) operating a chemical complex including in cooperative arrangement:
    a. at least two mixers for premixing an oxygen containing gas and a lower alkane containing gas to produce a mixed feedstock stream;
    b. at least one oxidative dehydrogenation reactor; and
    c. a feedline connecting each of the at least two mixers to the at least one oxidative dehydrogenation reactor, wherein the feedlines are fitted with sprayers to introduce cleaning solvent to internal walls of the feedline,
  wherein the at least two mixers are connected by the feedline in parallel to the at least one oxidative dehydrogenation reactor so that either a first gas mixing unit or a second gas mixing unit is connected to the at least one oxidative dehydrogenation reactor during normal operations; or wherein the at least two mixers are connected in parallel to the at least one oxidative dehydrogenation reactor so that both the first gas mixing unit and the second gas mixing unit are operating and connected to the at least one oxidative dehydrogenation reactor during normal operations; and wherein an oxidative dehydrogenation catalyst contained within the at least one oxidative dehydrogenation reactor reacts with the mixed feed stock stream to produce a product stream including the corresponding alkene;

ii) monitoring the pressure within the chemical complex during normal operation;

iii) introducing cleaning solvent into the feedline through the sprayer to remove sulfur containing deposits when a pressure drop is observed in the chemical complex;

iv) continuing to monitor the pressure within the chemical complex during operations and while cleaning solvent is being introduced;

v) stop cleaning solvent flow once the pressure in the chemical complex returns to normal operating levels.

In some embodiments, additional components or additives may be included in the cleaning solvent. For example, in some embodiments, sodium bisulfate is introduced with the cleaning solvent. In some embodiments, sodium bisulfate is added to DMDS and used as the cleaning solvent.

Additional Units in the ODH Chemical Complex

An example of a chemical complex useful with embodiments disclosed herein, shown schematically in FIG. 3, includes, in cooperative arrangement, an ODH reactor 101, a quench tower 102, an amine wash tower 103, a drier 104, a distillation tower 105, and an oxygen separation module 106. ODH reactor 101 includes an ODH catalyst capable of catalyzing, in the presence of oxygen which may be introduced via oxygen line 107, the oxidative dehydrogenation of a lower alkane introduced via alkane line 108. The ODH reaction may also occur in the presence of an inert diluent, such as carbon dioxide, nitrogen, or steam, that is added to ensure the mixture of oxygen and hydrocarbon are outside of flammability limits. Determination of whether a mixture is outside of the flammability limits, for the prescribed temperature and pressure, is within the knowledge of the skilled worker. An ODH reaction that occurs within ODH reactor 101 may also produce, depending on the catalyst and the prevailing conditions within ODH reactor 101, a variety of other products which may include carbon dioxide, carbon monoxide, oxygenates, and water. These products leave ODH reactor 101, along with unreacted alkane, corresponding alkene, residual oxygen, and inert diluent, if added, via ODH reactor product line 109.

ODH reactor product line 109 is directed to quench tower 102 which quenches the products from product line 109 and facilitates removal of oxygenates and water via quench tower bottom outlet 110. Unconverted lower alkane, corresponding alkene, unreacted oxygen, carbon dioxide, carbon monoxide, and inert diluent added to quench tower 102 exit through quench tower overhead line 111 and are directed into amine wash tower 103. Carbon dioxide present in quench tower overhead line 111 is isolated by amine wash tower 103 and captured via carbon dioxide bottom outlet 112 and may be sold, or, alternatively, may be recycled back to ODH reactor 101 as inert diluent (not shown). Products introduced into amine wash tower 103 via quench tower overhead line 111, other than carbon dioxide, leave amine wash tower 103 through amine wash tower overhead line 113 and are passed through a dryer 104 before being directed to distillation tower 105 via line 114, where C2/C2+ hydrocarbons are isolated and removed via C2/C2+ hydrocarbons bottom outlet 115. C2/C2+ hydrocarbons as used here in means hydrocarbons including at least two carbon atoms, including but not limited to ethane and ethylene, propane, propylene, and derivatives thereof, including, oxide, halide and amine derivatives. The remainder includes mainly C1 hydrocarbons, including remaining inert diluent and carbon monoxide, which leave distillation tower 105 via overhead stream 116 and is directed to oxygen separation module 106. As used herein, C1 hydrocarbons means methane and methane derivatives, including but not limited to carbon monoxide, carbon dioxide, and methanol.

Oxygen separation module 106 includes a sealed vessel having a retentate side 117 and a permeate side 118, separated by oxygen transport membrane 119. Overhead stream 116 may be directed into either of retentate side 117 or permeate side 118. Optionally, a flow controlling means may be included that allows for flow into both sides at varying levels. In that instance an operator may choose what portion of the flow from overhead stream 116 enters retentate side 117 and what portion enters permeate side 118. Depending upon conditions, an operator may switch between the two sides, allow equivalent amounts to enter each side, or bias the amount directed to one of the two sides. Oxygen separation module 106 also includes air input 120 for the introduction of atmospheric air, or other oxygen containing gas, into the retentate side 117. Combustion of products introduced into retentate side 117, due to the introduction of oxygen, may contribute to raising the temperature of oxygen transport membrane 119 to at least 850° C. so that oxygen can pass from retentate side 117 to permeate side 118. Components within the atmospheric air, or other oxygen containing gas, other than oxygen, cannot pass from retentate side 117 to permeate side 118 and can leave oxygen separation module 106 via exhaust 121.

As a result of oxygen passing from retentate side 17 to permeate side 18, there is separation of oxygen from atmospheric air, or other oxygen containing gas, introduced into retentate side 117. The result is production of oxygen enriched gas on permeate side 118, which is then directed via oxygen enriched bottom line 122 to ODH reactor 101, either directly or in combination with oxygen line 107. When overhead stream 116 is directed into retentate side 117 the degree of purity of oxygen in oxygen enriched bottom line 122 can approach 99%. Conversely, when overhead stream 116 is directed into permeate side 118 the degree of purity of oxygen in oxygen enriched bottom line 122 is lower, with an upper limit ranging from 80-90% oxygen, the balance in the form of carbon dioxide, water, and remaining inert diluent, all of which do not affect the ODH reaction as contemplated by the present disclosure and can accompany the enriched oxygen into ODH reactor 101. Water and carbon dioxide are ultimately removed by quench tower 102 and amine wash tower 103, respectively. In some embodiments, one of the advantages is that carbon dioxide can be captured for sale as opposed to being flared where it contributes to greenhouse gas emissions. Alternatively, when carbon dioxide is used as the inert diluent, any carbon dioxide captured in the amine wash can be recycled back to ODH reactor 101 to perform its role as inert diluent.

Oxygen transport membrane 119 is temperature dependent, allowing transport of oxygen when the temperature reaches at least 850° C. In some instances, the components in overhead stream 116 by themselves are not capable, upon combustion in the presence of oxygen, to raise the temperature of oxygen transport membrane 119 to the required level. For this reason, the chemical complex disclosed herein also includes fuel enhancement line 123, upstream of oxygen separation module 106, where combustible fuel, for example methane, may be added to supplement the combustible products from overhead stream 116.

As previously noted, a concern for ODH is the mixing of a hydrocarbon with oxygen. Under certain conditions the mixture may be unstable and lead to an explosive event. In one embodiment a lower alkane containing gas is mixed with an oxygen containing gas in a flooded mixing vessel. By mixing in this way pockets of unstable compositions are surrounded by a non-flammable liquid so that even if an ignition event occurred it would be quenched immediately. Provided addition of the gases to the ODH reaction is controlled so that homogeneous mixtures fall outside of the flammability envelope, for the prescribed conditions with respect to temperature and pressure, the result is a safe homogeneous mixture of hydrocarbon and oxygen.

In some embodiments, there is at least two flooded gas mixer units upstream of the ODH reactor. However, any suitable gas mixing unit may be duplicated or twinned and used in the chemical complex as disclosed herein.

The temperature of the contents within product line 109 in a typical ODH process can reach 450° C. It may be desirable to lower the temperature of the stream before introduction into quench tower 102. In that instance the use of a heat exchanger immediately downstream of each ODH reactor and immediately upstream of the quench tower 102 is contemplated. Use of heat exchanger to lower temperatures in this fashion is well known in the art.

Also contemplated herein is the use of various tools commonly used for chemical reactors, including flowmeters, compressors, valves, and sensors for measuring parameters such as temperature and pressure. It is expected that the person of ordinary skill in the art would include these components as deemed necessary for operation or for compliance with legal obligations related to safety regulations.

ODH Reactor

The present disclosure contemplates the use of any of the known reactor types applicable for the ODH of hydrocarbons. One example is the conventional fixed bed reactor. In a typical fixed bed reactor, reactants are introduced into the reactor at one end, flow past an immobilized catalyst, products are formed and leave at the other end of the reactor. Designing a fixed bed reactor suitable for use can follow techniques known for reactors of this type. A person skilled in the art would know which features are required with respect to shape and dimensions, inputs for reactants, outputs for products, temperature and pressure control, and means for immobilizing the catalyst.

In some embodiments, the ODH reactor includes a fixed bed reactor.

In other embodiments, the ODH reactor includes a tube in shell heat exchanger fixed bed type reactor.

Also contemplated is the use of a fluidized bed reactor. These types of reactors are also well known. Typically, the catalyst is supported by a porous structure, or distributor plate, located near a bottom end of the reactor and reactants flow through at a velocity sufficient to fluidize the bed (e.g. the catalyst rises and begins to swirl around in a fluidized manner). The reactants are converted to products upon contact with the fluidized catalyst and subsequently removed from the upper end of the reactor. Design considerations include shape of the reactor and distributor plate, input and output, and temperature and pressure control, all of which would fall under knowledge of the person skilled in the art.

In another embodiment, the ODH reactor includes a fluidized bed reactor.

The present disclosure also contemplates multiple ODH reactors, either in series or in parallel. A swing bed type reactor is also envisioned in some embodiments. In this instance parallel beds are alternatively exposed to a hydrocarbon feed including mainly hydrocarbons with optional residual oxygen, or an oxygen feed that is hydrocarbon free. The oxygen feed is directed to one reactor to re-oxidize a spent catalyst while simultaneously the hydrocarbon feed is passed through the other bed containing active oxidized catalyst, allowing ODH to occur. A valve configuration allows swinging the oxygen and hydrocarbon feeds between the two beds to regenerate the oxidized catalyst in one bed while ODH is occurring in the other bed. Use of multiple reactors, including ODH reactors, in either a parallel, series, or swing bed type arrangement is well known in the art.

In another embodiment, the ODH reactor includes multiple inlets for introduction of an oxygen containing gas. In this embodiment, oxygen addition is distributed in a staged manner throughout the reactor, limiting peak temperature increases by leveling oxygen concentration through the height or length of the reactor.

U.S. Pat. No. 9,545,610, entitled "Complex Comprising Oxidative Dehydrogenation Unit", inventor Simanzhenkov, describes an ODH reactor where oxygen permeable ceramic tubes are placed inside of shell. In the description, the patent describes how ethane flows through the tube, while oxygen flows between the tubes and the outer shell. Oxygen can pass through the ceramic wall holding the catalyst, allowing conversion of ethane to ethylene at the interface between the ceramic wall and the interior of the tube. Ceramics are brittle by nature, and need to be reinforced or protected. This may be accomplished by incorporation of steel mesh on the interior and exterior surfaces of the ceramic tubes. This design provides the advantage that when a ceramic membrane loses integrity only excess oxygen enters that tube. Oxygen detectors located at the exit of each tube can detect the presence of excess oxygen, indicating the loss of integrity. The reactor can then be shut down safely and the damaged tube located and repaired. The present disclosure contemplates the use of this reactor design.

In some embodiments, the ODH reactor includes an outer shell and one or more internal ceramic tubes defining a separate flow passage for ethane down the interior of the tubes and an annular passage between the external shell of the reactor and the ceramic tubes defining a flow path for an oxygen containing gas.

In some embodiments, the ceramic tubes further include an internal steel mesh and an external steel mesh.

ODH Catalyst

There are a number of catalysts which may be used in accordance with the present disclosure. The following catalyst systems may be used individually or in combination. One of ordinary skill in the art would understand that combinations should be tested at a laboratory scale to determine if there are any antagonistic effects when catalyst combinations are used.

The oxidative dehydrogenation catalyst disclosed herein may be chosen from:

i) catalysts of the formula:

$$Mo_aV_bTe_cNb_dPd_eO_f$$

wherein a, b, c, d, e and f are the relative atomic amounts of the elements Mo, V, Te, Nb, Pd and O, respectively; and when a=1, b=0.01 to 1.0, c=0.01 to 1.0, d=0.01 to 1.0, 0.00≤e≤0.10 and f is dependent on the oxidation state of the other elements, i.e. f is a number to satisfy the valence state of the catalyst;

ii) catalysts of the formula:

$$Ni_g A_h B_i D_j O_f$$

wherein: g is a number from 0.1 to 0.9, for example from 0.3 to 0.9, or for example from 0.5 to 0.85, or for example 0.6 to 0.8; h is a number from 0.04 to 0.9; i is a number from 0 to 0.5; j is a number from 0 to 0.5; f is a number to satisfy the valence state of the catalyst; A is chosen from Ti, Ta, V, Nb, Hf, W, Y, Zn, Zr, Si and Al or mixtures thereof; B is chosen from La, Ce, Pr, Nd, Sm, Sb, Sn, Bi, Pb, Tl, In, Te, Cr, Mn, Mo, Fe, Co, Cu, Ru, Rh, Pd, Pt, Ag, Cd, Os, Ir, Au, Hg, and mixtures thereof; D is chosen from Ca, K, Mg, Li, Na, Sr, Ba, Cs, and Rb and mixtures thereof; and O is oxygen;

iii) catalysts of the formula:

$$Mo_a E_k G_l O_f$$

wherein E is chosen from Ba, Ca, Cr, Mn, Nb, Ta, Ti, Te, V, W and mixtures thereof; G is chosen from Bi, Ce, Co, Cu, Fe, K, Mg V, Ni, P, Pb, Sb, Si, Sn, Ti, U and mixtures thereof; a=1; k is 0 to 2; l is 0 to 2, with the proviso that the total value of l for Co, Ni, Fe and mixtures thereof is less than 0.5; f is a number to satisfy the valence state of the catalyst;

iv) catalysts of the formula:

$$V_m Mo_n Nb_o Te_p Me_q O_f$$

wherein: Me is a metal chosen from Ta, Ti, W, Hf, Zr, Sb and mixtures thereof; m is from 0.1 to 3; n is from 0.5 to 1.5; o is from 0.001 to 3; p is from 0.001 to 5; q is from 0 to 2; and f is a number to satisfy the valence state of the catalyst; and v) catalysts of the formula:

$$Mo_a V_r X_s Y_t Z_u M_v O_f$$

wherein: X is at least one of Nb and Ta; Y is at least one of Sb and Ni; Z is at least one of Te, Ga, Pd, W, Bi and Al; M is at least one of Fe, Co, Cu, Cr, Ti, Ce, Zr, Mn, Pb, Mg, Sn, Pt, Si, La, K, Ag and In; a=1.0 (normalized); r=0.05 to 1.0; s=0.001 to 1.0; t=0.001 to 1.0; u=0.001 to 0.5; and v=0.001 to 0.3; and f is a number to satisfy the valence state of the catalyst.

The above catalysts may be used individually or in combinations. One of ordinary skill in the art would be aware to conduct routine tests to determine if there are antagonistic interactions between two or more catalyst which are being considered.

The methods of preparing the catalysts are known to those skilled in the art.

The present disclosure also contemplates that the ODH catalyst can be supported. There are several ways that the ODH catalyst may be supported, all of which are well known in the art.

In some embodiments, the support may have a low surface area, for example, less than 50 m²/g, or for example, less than 20 m²/g. The support may be prepared by compression molding. At higher pressures, the interstices within the ceramic precursor being compressed collapse. Depending on the pressure exerted on the support precursor, the surface area of the support may be from about 20 to 5 m²/g, or for example 18 to 10 m²/g.

There is a safety advantage using low surface area supports in that, in those embodiments, there is a reduced probability that an interstitial space may be filled only with oxidant providing a source of ignition.

The low surface area support could be of any conventional shape, such as, spheres, rings, saddles, etc. These types of supports would be used in more conventional reactors where a mixed stream or sequential stream of gaseous reactants pass over the supported catalyst and the ethane is converted to ethylene. There are a number of other approaches in the prior art where, for example, a mixed bed of supported catalyst and a reversible metal oxide may be passed together through a reaction zone to release oxide to the reaction and then regenerate the oxide. In some embodiments, the reversible metal oxide may contact a screen or permeable membrane having the supported catalyst on the other side together with a stream of ethane to release oxygen to the reaction.

In some embodiments, the catalyst may be supported on a surface of a permeable membrane defining at least part of the flow path for one reactant and the other reactant flows over the opposite surface of the ceramic to permit the oxidant and ethane to react on the ceramic surface.

In some embodiments, the support is dried prior to use. The support may be heated at a temperature of at least 200° C. for up to 24 hours, or for example, at a temperature from 500° C. to 800° C. for about 2 to 20 hours, or for example 4 to 10 hours. The resulting support will be free of adsorbed water and should have a surface hydroxyl content from about 0.1 to 5 mmol/g of support, for example, from 0.5 to 3 mmol/g of support.

The amount of the hydroxyl groups in silica may be determined according to the method disclosed by J. B. Peri and A. L. Hensley, Jr., in *J. Phys. Chem.*, 72 (8), 2926, 1968.

The dried support may then be compressed into the required shape by compression molding. Depending on the particle size of the support, it may be combined with an inert binder to hold the shape of the compressed part.

The support for the catalyst may be a ceramic or ceramic precursor formed from oxides, dioxides, nitrides, carbides and phosphates chosen from silicon dioxide, fused silicon dioxide, aluminum oxide, titanium dioxide, zirconium dioxide, thorium dioxide, lanthanum oxide, magnesium oxide, calcium oxide, barium oxide, tin oxide, cerium dioxide, zinc oxide, boron oxide, boron nitride, boron carbide, boron phosphate, zirconium phosphate, yttrium oxide, aluminum silicate, silicon nitride, silicon carbide and mixtures thereof.

In some embodiments, components for forming ceramic membranes include oxides of titanium, zirconium, aluminum, magnesium, silicon and mixtures thereof.

In some embodiments, the catalyst loading on the support provides from 0.1 to 20 weight % or for example from 5 to 15 weight %, or for example from 8 to 12 weight % of the catalyst and from 99.9 to 80 weight %, or for example, from 85 to 95 weight %, or for example, from 88 to 92 weight % of the support.

The catalyst may be added to the support in any number of ways. For example, the catalyst could be deposited from an aqueous slurry onto one of the surfaces of the low surface area support by impregnation, wash-coating, brushing or spraying. The catalyst could also be co-precipitated from a slurry with the ceramic precursor (e.g., alumina) to form the low surface area supported catalyst.

The support and catalyst may be combined and then comminuted to produce a fine particulate material having a particle size ranging from 1 to 100 micron. The comminution process may be any conventional process including ball and bead mills, both rotary, stirred and vibratory, bar or tube mills, hammer mills, and grinding discs. In some embodiments, the method of comminution is a ball or bead mill.

The particulate catalyst may be used in an ODH reactor which may include single or multiple beds.

By-Product Removal

Oxidative dehydrogenation of alkanes inevitably produces not only corresponding alkenes, but other by-products as well. Depending on the conditions, including the catalyst type, the levels of by-products present downstream can range from minimal (less than 2%), to significant (greater than 2%). Even at minimal levels by-products are undesirable as they may interfere with downstream applications where the produced alkene is utilized. For ODH of lower alkanes, for example ethane, the most common by-products include carbon oxides, including carbon monoxide and carbon dioxide, oxygenates, and water.

In some embodiments, the separation of oxygenates and water from an ODH reactor product stream is achieved using a quench tower. Oxygenates refer to by-products of the oxidative dehydrogenation process that contain carbon, hydrogen, and oxygen, and include, but are not limited to, acetic acid, acrylic acid, and maleic acid. While the primary purpose of a quench tower is the cooling of a gaseous product stream, there is a secondary benefit for the purposes disclosed herein. Cooling of the gaseous product line after leaving the reactor promotes condensation of water and oxygenates which can then be separated from the components that remain in the gaseous phase, namely the lower alkane, its corresponding alkene, and any carbon oxides. Some quench towers involve the spraying of water, or other liquid in which oxygenates are soluble, from the top of the tower onto the product stream entering from the bottom of the tower. Contact with water promotes cooling and ultimately condensation of the heavier components slated for removal.

In some embodiments, a product stream containing unconverted alkane, corresponding alkene, residual oxygen and by-products are passed through a quench tower to remove water and oxygenates. The remainder is passed on for the next step of purification. Techniques of this nature have been thoroughly developed and are commonplace in the prior art. The person skilled in the art would understand how to integrate a quench tower into the chemical complex disclosed herein.

Also contemplated is the use of multiple quench towers. Where multiple ODH reactors are employed, in some embodiments, it is preferred that each ODH reactor is followed by a quench tower, for example, in instances where the reactors are in series. In this setting, oxygenates and water are removed before the remainder, optionally supplemented with additional oxygen, is passed on to the next ODH reactor in the series. In a parallel arrangement the product streams from the parallel reactors may be combined before introduction into a quench tower.

Another common and well known separation method is the use of alkylamines, referred to herein as amines, in a scrubber to remove carbon dioxide from gaseous compositions. Carbon dioxide present in a gas is absorbed by aqueous amine solution which can then be separated from the remaining gaseous components. The amine is stripped of carbon dioxide by heating above 100° C. and recycled to continue the process, while water from the stripper vapor is condensed, leaving relatively pure carbon dioxide. The carbon dioxide, highly concentrated, can be captured and sold, or, alternatively it can be recycled back to act as an inert diluent for the lower alkane and oxygen containing gases when introduced into the ODH reactor. This is one advantage disclosed herein. Carbon dioxide produced in the process can be captured instead of being flared where it contributes to greenhouse gas emissions. This becomes more relevant with the addition of the oxygen separator which also produces carbon dioxide.

Amine scrubbing has been used, for example in the petrochemical industry, for over sixty years. Consideration of the type of amines used in the process requires some attention. Amines used vary in their ability to remove oxygen and in their tendency to promote the formation of degradation products. For example, monoethanolamine (MEA) is commonly used and is capable of removing a high percentage of carbon dioxide, even at low concentrations, but can also react with the carbon dioxide to form degradation products. This results in lower carbon dioxide capture and a reduction of available amines for subsequent absorption cycles.

The stream leaving the amine wash tower includes unconverted lower alkane, corresponding alkene, and carbon monoxide, and possibly methane as a contaminant present in the original hydrocarbon feedstock. Inert diluent other than carbon dioxide, if used, may also be present in the stream leaving the amine wash tower. The stream leaving the amine wash tower will also likely contain water—carryover from the amine wash tower—that should be removed via a dryer prior to directing the stream to a distillation tower. When cryogenic distillation is employed any water present in the stream may freeze in the distillation tower, causing problems related to plugging and fouling of the tower. Dehydration of gaseous compositions using a dryer is well known in the art. Methods include, but are not limited to, absorption using a sorbent such as triethyleneglycol (TEG), adsorption with at least two solid desiccant containing adsorption beds, and condensation. The product stream will contain less than 50 ppm of water, or for example less than 25 ppm of water, of for example less than 10 ppm of water, before being passed on to the next stage.

After removal of water, further separation of the product stream into an overhead stream and a C2/C2+ hydrocarbons stream using a distillation tower is contemplated. The overhead steam includes mainly C1 hydrocarbons (hydrocarbons with only one carbon), including mostly carbon monoxide but with the possibility of smaller amounts of methane, and inert diluent if used. The C2/C2+ hydrocarbons stream would include the unconverted lower alkane and its corresponding alkene, and any additional hydrocarbons (hydrocarbons containing 2 or more carbons), that were present as impurities in the original hydrocarbon feedstock added to the ODH reactor. Using a distillation tower for separation of C1 hydrocarbons and C2/C2+ hydrocarbons is well known in the art, and employs heating and cooling of gases in the presence of trays which capture condensed species. The spacing and number of trays dictate the degree of separation.

In some embodiments, the distillation tower includes an upper outlet for removal of the overhead stream, and a lower outlet for removal of the remainder, including the higher weight C2/C2+ hydrocarbons. The overhead stream is directed toward the next step in the chemical complex disclosed herein, the oxygen separation module. The C2/C2+ hydrocarbons can then be directed to a C2+ splitter to separate the lower alkane from its corresponding alkene. The lower alkane can be fed back to the ODH reactor, and the corresponding alkene, the target product, can be captured and employed for use in a variety of applications that depend on the nature of the alkene. For example, if the desired product is ethylene then use in synthesis of polyethylene would be appropriate.

As mentioned, the degree of separation capable within a distillation tower is dependent upon the number of trays within the unit. The most common method involves cryogenic distillation so the nature of the species targeted for separation and their relative volatilities plays a role. For example, the relative volatility of ethylene to ethane is quite small. As a result, a tower designed to separate the two species would need to be tall and include a large number of trays. The difference in relative volatilities between C2/C2+ hydrocarbons and C1 hydrocarbons is significant enough that a smaller tower with fewer trays would suffice. A person skilled in the art would understand from this relationship that a smaller tower would be sufficient to separate out carbon monoxide and methane (C1 hydrocarbons), from the unconverted lower alkane and its corresponding alkene. However, if separation of the lower alkane with the corresponding alkene is also desired then a much larger tower would be needed. In that case, the tower would include another outlet, or side out where the corresponding alkene may be withdrawn from the distillation tower. Also contemplated is the separation of the lower alkane and corresponding alkene in a separate unit, after removal of the lower alkane and corresponding alkene from the distillation tower. Specifically, a splitter, which is well known in the art, may be used. In some embodiments, the stream of C2/C2+ hydrocarbons leaving the distillation tower is directed into a splitter.

In some embodiments, a distillation tower includes an outlet for removal of the overhead stream and an outlet for removal of the C2/C2+ hydrocarbons stream. In other embodiments the distillation tower includes a side outlet for removal of alkenes.

Oxygen Separation Module

In embodiments that employ an oxygen separation module, that module includes a sealed vessel with two compartments, separated by a temperature dependent oxygen transport membrane. The two compartments are the retentate side and the permeate side. That the membrane is temperature dependent means that when at a critical temperature the membrane will selectively allow oxygen to pass through from one side to the other. The oxygen separation module also includes at least two inlets, air input for introducing atmospheric air into the retentate side and the other for introducing overhead stream into either of the retentate side or the permeate side, or both retentate side and permeate side. Finally, there are two outputs from the oxygen separation module. There is exhaust for removal of oxygen depleted air and combustion products from the retentate side, and an outlet for removal of oxygen enriched gas and possibly combustion products from the permeate side into oxygen enriched bottom line. The oxygen enriched gas, and possibly combustion products, may be recycled back as or part of the oxygen containing gas introduced into the ODH reactor.

In some embodiments, the oxygen separation module is a tube. In some embodiments, the oxygen transport membrane is also a tube and fits inside a larger tube which forms the outer wall of oxygen separation module. The annular space between the larger tube and oxygen transport membrane corresponds to the retentate side, while the space within oxygen transport membrane corresponds to the permeate side. Material suitable for construction of the outer wall include those resistant to temperatures that exceed 850° C. and approach 1,000° C., selection of which falls within the knowledge of the skilled worker.

In some embodiments, the inlet for the overhead stream enters the oxygen transport module into either of the permeate side or the retentate side. In some embodiments, a valve for switching between directing the overhead stream to the retentate side or the permeate side is present. This would allow an operator to choose which of the sides, permeate or retentate, that the overhead stream is directed to.

Finally, in some embodiments, introducing the overhead stream into both the retentate side and permeate side simultaneously is contemplated. This includes the ability to alter the relative amount of overhead stream which is entered into each side. For example, an operator may choose to permit 80% of the overhead stream to enter into the retentate side and 20% to the permeate side, or vice versa. To be clear, the amount of the overhead stream that enters either side, permeate or retentate, can range from 0-100%, with the fraction for each side totaling 100%. Precision valves that can control the flow sent to either side are well known in the art, and include, without limitation, solenoid valves, ball valves, or a combination of a backpressure needle valve and solenoid valve.

The oxygen transport membrane component of the oxygen transport module selectively allows passage of oxygen when the membrane reaches a critical temperature. Membranes of this nature are known. Specifically, a Mixed Ionic-Electronic Conducting (MIEC) membrane is contemplated for use with the present disclosure. Movement of oxygen across the membrane is driven by an oxygen partial pressure gradient, moving from the high oxygen partial pressure side to the low oxygen partial pressure side. To get the oxygen to move to the permeate side a skilled operator would understand that the partial pressure of oxygen on the retentate side would need to be increased to the point where it equals or exceeds the partial pressure of oxygen on the permeate side. For example, if oxygen on the permeate side is close to 100% of the volume at a pressure of the 1 atm, then the pressure on the retentate side would need to be increased to at least 5 atm when atmospheric air is added and contains approximately 21% oxygen by volume. Alternatively, the pressure on the permeate side could be reduced to levels at or below 0.2 atm using a vacuum driven process.

Also contemplated in the design of the oxygen separation module is the ability to add a sweep gas, such as steam or carbon dioxide, to the permeate side to dilute oxygen that crosses over from the retentate side. The effect of the sweep gas is the lowering of the oxygen partial pressure on the permeate side to drive diffusion of oxygen from the retentate side. A result of this configuration is a much lower percentage of oxygen within the oxygen enriched bottom line, as it is diluted by the sweep gas. Theoretically, the oxygen percentage could drop well below 10%. However, if water is the sweep gas, then a heat exchanger downstream of oxygen separation module can be used to remove the water following condensation, increasing the relative amount of oxygen in the line. If carbon dioxide is used, then an operator can determine the amount required to produce the desired oxygen level in the oxygen enriched bottom line. By altering the amount of sweep gas an operator can control how much oxygen is present in the line as it leaves the oxygen separation module. A person skilled person in the art would understand this relationship and would be familiar with using a sweep gas and with using means for controlling the pressure in a sealed vessel such as the type contemplated for the oxygen separation module disclosed herein.

It is well known that oxygen flux across the membrane is dependent upon the thickness of the membrane. A thin membrane allows oxygen to cross more quickly than a thick membrane. A membrane comprised of a single layer, or monolithic type membrane, may be reduced in thicknesses in the range of 0.1 to 0.2 µM to allow greater oxygen flux. However, these thicknesses are not practical due to susceptibility to mechanical instability. If a monolithic membrane is to be used, thicknesses below 0.2 mm are not recommended. Other known membrane configurations include asymmetric membranes where a very thin conducting layer is supported on both sides by a porous structure. This allows a user to employ very thin membranes that allow higher oxygen flux without sacrificing stability. It is not essential to use any particular membrane structure provided the oxygen flux across the membrane is sufficient. In some embodiments, the oxygen transport membrane has an oxygen flux within the range of 300-1500 l/hr*m$^2$, or for example from 500-1300 l/hr*m$^2$, or for example from 700-1000 l/hr*m$^2$.

Theoretically, the oxygen transport membrane can reach 850° C. due to the exothermic nature of combustion of the C1 hydrocarbons present in the overhead stream. However, in instances where the C1 hydrocarbons as a sole source of feedstock for combustion are insufficient to reach the required temperature, the present disclosure contemplates the addition of combustible fuel to the oxygen separation module or the inclusion of an independent means for heating the oxygen separation module, including the oxygen transport membrane. For instance, a separate line may add a combustible fuel, for example methane, either into the overhead stream before entering the oxygen separation module, or directly into the oxygen separation module. Alternatively, a heat exchanger or other means may be employed to heat the module to the required temperature. In some embodiments, it is preferred that when using a heat exchanger or other means for heating that heat is distributed evenly throughout the module. Also contemplated is heating the overhead stream just upstream of the oxygen separation module.

During start-up of the chemical complex the oxygen transport membrane may not be at the required temperature. As a result, oxygen from the injected air cannot pass into the permeate side. In this instance it would be preferable to direct the overhead stream solely into the retentate side so that combustion on that side can contribute to increasing the temperature of the oxygen transport membrane to the point where oxygen can cross. When at the steady state and the temperature of the oxygen transport membrane exceeds 850° C. the overhead stream may be directed to either side because oxygen can freely pass and permit combustion such that heat is continuously generated. Alternatively, during startup, other means, such as a heat exchanger, may be used to heat the membrane.

ODH Process

Use of the ODH reactor as described in the chemical complex disclosed herein falls within the knowledge of the person skilled in the art. For best results, the oxidative dehydrogenation of a lower alkane may be conducted at temperatures from 300° C. to 550° C., or from 300° C. to 500° C., or for example, from 350° C. to 450° C., at pressures from 0.5 to 100 psi (3.447 to 689.47 kPa), or for example, from 15 to 50 psi (103.4 to 344.73 kPa), and the residence time of the lower alkane in the reactor is typically from 0.002 to 30 seconds, or for example from 1 to 10 seconds.

The lower alkane containing gas is for example of a purity greater than 95%, or for example, 98%. In some embodiments, the process includes the addition of an ethane containing of purity of 95%, or for example, 98%.

In some embodiments, the process has a selectivity for the corresponding alkene (ethylene in the case of ethane ODH) of greater than 95%, or for example, greater than 98%. The gas hourly space velocity (GHSV) will be from 500 to 30,000 h$^{-1}$, or for example greater than 1000 h$^{-1}$. The space-time yield of corresponding alkene (productivity) in g/hour per kg of the catalyst should be not less than 900, or for example, greater than 1,500, or for example, greater than 3,000, or for example, greater than 3,500 at 350 to 400° C. It should be noted that the productivity of the catalyst will increase with increasing temperature until the selectivity is sacrificed.

When the lower alkane is ethane, the specificity of conversion to ethylene should be not less than 80%, or for example, greater than 90%, or for example, 95% or greater.

The ratio of oxygen to lower alkane added to the ODH reactor may also effect the composition and contribution of by-products to the product stream leaving the ODH reactor. Excess oxygen may oxidize the corresponding alkene to a carboxylic acid. For example, ethylene produced in the ODH reactor may be further oxidized to acetic acid. Depending upon the desired product this may be desirable. A skilled operator would understand how changing the ratio of added gases, in combination with ODH catalyst selection, alters the products present in the stream leaving the ODH reactor.

Removal of by-products such as oxygenates, for example acetic acid, is routine for operators skilled in these types of processes. The quench tower, which is primarily used to reduce the temperature of the product stream, may be used to isolate oxygenates and water produced in the ODH reactor. The cooling of the product stream results in condensation of oxygenates at a much higher temperature than the dew point of the alkane, corresponding alkene gases. By taking advantage of this difference operators may capture the condensed products and allow the gaseous remains to move on to the next step in the separation of by-products from the product stream. Captured oxygenates may be used in other well-known downstream processes. For example, in ODH of ethane to ethylene, the ethylene may be further oxidized to acetic acid, which may be reacted with ethylene to produce vinyl acetate or other oxygenates.

Also contemplated is the addition of low pH compounds to the quench tower which has the effect of improving removal of oxygenates. In the absence of addition of low pH compounds, it is possible that not all oxygenates will undergo condensation within the quench tower. In this case, any gaseous residual oxygenates may be passed on to the next stage. Addition of a low pH compound, such as sodium bicarbonate, may promote conversion of oxygenates into compounds with a higher dew point, increasing the likelihood of condensation.

Removal of carbon dioxide from the product stream, in combination with the oxygen separation module, is one of the advantages disclosed herein. Carbon dioxide produced in the oxygen separation module, due to combustion on the permeate side of the oxygen transport membrane, can be captured, instead of being released to the atmosphere. The oxygen enriched gas and associated combustion products that are recycled back re-enter the chemical complex so that any carbon dioxide present can be isolated in the amine wash. Furthermore, in some embodiments, the present disclosure also contemplates recycling the carbon dioxide isolated by the amine wash back to the ODH reactor where it can be used as the inert diluent.

While ODH doesn't produce significant amounts of carbon dioxide, it does produce carbon monoxide, which ordinarily would be flared into the atmosphere when the opportunity to convert the carbon monoxide to value added chemicals is not feasible at the manufacturing site. In some embodiments, the combustion of the carbon monoxide is allowed in a system that captures the resulting carbon dioxide and shuttles it back through the ODH chemical complex where it can be captured.

It should be noted that, theoretically, removal of oxygenates and carbon dioxide prior to oxygen separation is not essential. It is conceivable to pass the product stream from the ODH reactor directly to an oxygen separation module. However, in this instance the target alkene would be subjected to combustion and lost, which, in some embodiments, may defeat the purpose of the ODH reaction. In some embodiments, it may be necessary to separate the target alkene prior to oxygen separation. The present disclosure includes separation of unconverted alkane and corresponding alkene from the lighter C1 hydrocarbons using a cryogenic distillation process. The presence of oxygenates, such as acetic acid, and carbon dioxide would severely impact the function of a cryogenic distillation process. For this reason, the removal of oxygenates and carbon dioxide is preferred in some embodiments.

The amine wash results in addition of water into the product stream, which should be removed prior to distillation. As previously discussed dehydration of gaseous compositions falls within the common general knowledge of those skilled in the art.

Distillation of gaseous products and separation of components is also well known in the art. The skilled worker would know how to use a distillation tower to separate C1 hydrocarbons from C2/C2+ hydrocarbons.

The process of ODH as it relates to oxygen separation may vary, in some embodiments, dependent upon the temperature of the oxygen transport membrane. When the oxygen transport membrane is below the temperature at which oxygen can selectively pass through, the overhead stream may be directed into the retentate side, where atmospheric air is introduced. In this situation the oxygen within the air is present for the combustion of the C1 hydrocarbons present in the overhead stream. An operator makes the judgement of whether the degree to which this combustion raises the temperature of the oxygen transport membrane is significant enough for selective oxygen transport to occur. If it is insufficient, meaning the temperature does not surpass 850° C., regardless of the amount of C1 hydrocarbon gas flowing into the module, then additional combustible fuel may be added. For example, adding methane to the overhead stream may be sufficient to reach the desired temperature.

Provided enough combustion is occurring with addition of combustible fuel and the temperature of the membrane is above 850° C. then, in some embodiments, the combustible fuel or the overhead stream may be directed into the permeate side. The reason this is possible is that since the membrane is hot enough, oxygen can pass through and act on the C1 hydrocarbons present in the overhead stream and added to the permeate side, releasing heat so as to maintain the membrane in an oxygen transportable mode. Where the overhead stream is directed to depends on the desired degree of oxygen separation. When directed to the retentate side, combustion results in production of water and carbon dioxide, which cannot pass through and are therefore ejected through the exhaust. In this mode, it is not possible to capture the carbon dioxide produced in the chemical complex described. There are other modes for capture that may be involved but are not integrated into the ODH chemical complex. The oxygen that passes in this configuration is unaccompanied by the combustion products and therefore is of very high purity. In some embodiments, the overhead stream is directed to the retentate side and the oxygen enriched stream includes at least 95% oxygen, or for example 98% oxygen, or for example 99% oxygen.

In the alternative, the overhead stream may be directed into the permeate side. In this setting the oxygen transport membrane is at the required temperature. In this case the C1 hydrocarbons within the overhead stream and added to the permeate side are subjected to combustion with the oxygen crossing the membrane. Any unreacted oxygen and the combustion products are mixed before leaving. As a result, the oxygen is diluted and the oxygen enriched stream contains a lower degree of oxygen. The degree of oxygen dilution may also be significantly increased when a sweep gas is employed, even approaching levels below 10%. In some embodiments, the overhead stream is directed to the permeate side and the oxygen enriched stream includes at least 20% oxygen, or for example 55% oxygen, or for example 90% oxygen, with the balance including carbon dioxide and water, and possibly inert diluent.

Optimization of the process requires an operator to understand that the side to which the overhead stream is directed will impact on the fate of carbon dioxide produced and the degree to which carbon dioxide contributes to the oxygen enriched gas directed back. Since carbon dioxide is a suitable inert diluent for dilution of the lower alkane and oxygen containing gases it is expected that an operator may adjust the ratio of overhead stream entering into the retentate side relative to the permeate side so as to produce an oxygen enriched gas with a desired level of carbon dioxide. Ideally, the level will be adjusted so that when combined with carbon dioxide isolated by the amine wash the total amount will equal the amount required for dilution of the lower alkane and oxygen containing gases while at the same time minimizing the amount of carbon dioxide released into the atmosphere after ejection from the oxygen separation module exhaust.

In some embodiments, the entirety of the carbon dioxide isolated in the amine wash is recycled back as inert diluent and the ratio of the overhead stream entering the retentate side relative to the permeate side is altered to allow for production of oxygen enriched gas with a degree of carbon dioxide that when mixed with carbon dioxide from the amine wash falls within the levels required for a safe mixture with the lower alkane containing gas.

The present invention will further be described by reference to the following examples. The following examples are merely illustrative of the invention and are not intended to be limiting. Unless otherwise indicated, all percentages are by weight.

Examples

In an experiment to find an effective solvent that could dissolve sulfur fouling. The following chemicals were tested experimentally:
 1. Toluene*
 2. Methanol
 3. Wash Oil* (Refinery Heavy Reformate—Aromatic hydrocarbons)
 4. Heptane
 5. Water
 6. EnviroSol (Citrus based solvent/degreaser)
 7. Dimethyl sulfoxide (DMSO)
 8. Carbon disulfide (CS2)
 9. Dimethyl disulfide* (DMDS)
 10. Tertiary Butyl Polysulfide (TBPS)

CS2 was found to be a good solvent for removing fouling material at room temperature, however this solvent presents a safety hazard and has very high toxicity. Additionally, its effect on the ODH process is unknown.

Heated toluene was also found to be effective and is a safer solvent than CS2. As a result, heated toluene has been recommended for use under extreme circumstances. For example, when the feed vaporizers are blown down the material is pushed into the flare header where it could accumulate and block the line. As this also presents some safety hazards and could lead to a full site shutdown, the plant could inject toluene into the flare and heat the piping using external steam hoses. However, using a heated solvent to remove sulfur-based fouling can lead to precipitation down the line once the solvent cools. The entire line should be warmed up to prevent this issue.

Due to the above challenges an alternative solution was sought for. It was found in literature that heated DMDS may be a good material to dissolve solid sulfur fouling as it may not act as a true solvent, but rather as a reactant. Without wishing to be bound by theory, it is believed that the sulfur fouling enters an equilibrium with the DMDS solvent which allows it to remain in the liquid phase regardless of temperature. It is stated in literature that DMDS is capable of taking up as much as 600 wt. % of elemental sulfur as polysulfides at 80° C.

Testing was completed in the laboratory, using the fouling collected from the feed vaporizer and heated DMDS. Approximately 1 g of fouling was submerged in 10 g of DMDS. The mixture was heated to 80° C., after approximately 30 minutes the solid material was completely dissolved and separated into a dark black liquid phase and a yellow liquid phase. The material was removed from the heat and left overnight at room temperature, upon further inspection it was verified that the material remained in liquid form and no solid fouling was present. Since a decrease in temperature typically favors precipitation, the vial was then cooled to approximately −60° C. using dry ice. At such low temperatures it was found that the entire mixture would become a gel-like solid. Once the vial was removed from the cooling medium and allowed to return to room temperature the material became a liquid once again The majority of the solvents listed above were tested at room temperature for extended periods of time (20 hours for solvents 1-6 and 1 hour for sulfur-based solvents 7-10) additionally, solvents marked with an asterisk (*) were also tested at high temperatures (up to 80° C.).

Overall, the majority of the solvents were not effective in dissolving the sulfur-based fouling. The noted exceptions were carbon disulfide at room temperature, toluene at high temperatures, and DMDS at high temperatures.

Example #2: Effect of DMDS on Catalyst Performance

Using a Micro Reactor set up Catalyst long term activity testing using fixed bed reactor platform on Micro Reactor Unit 1 was conducted to test the robustness of the ODH catalysts continuously for 10 days for DMDS effect study. This test was carried out with consistent run condition with temperature of 369° C. and 3000 h-1 space velocity (140 sccm of 18% O2/82% ethane) to aim for 25% conversion. Also, the regeneration condition was 380 C with air flow of 250 sccm for 3 hours each time the regeneration is shown on the FIG. 4.

Figure 4:
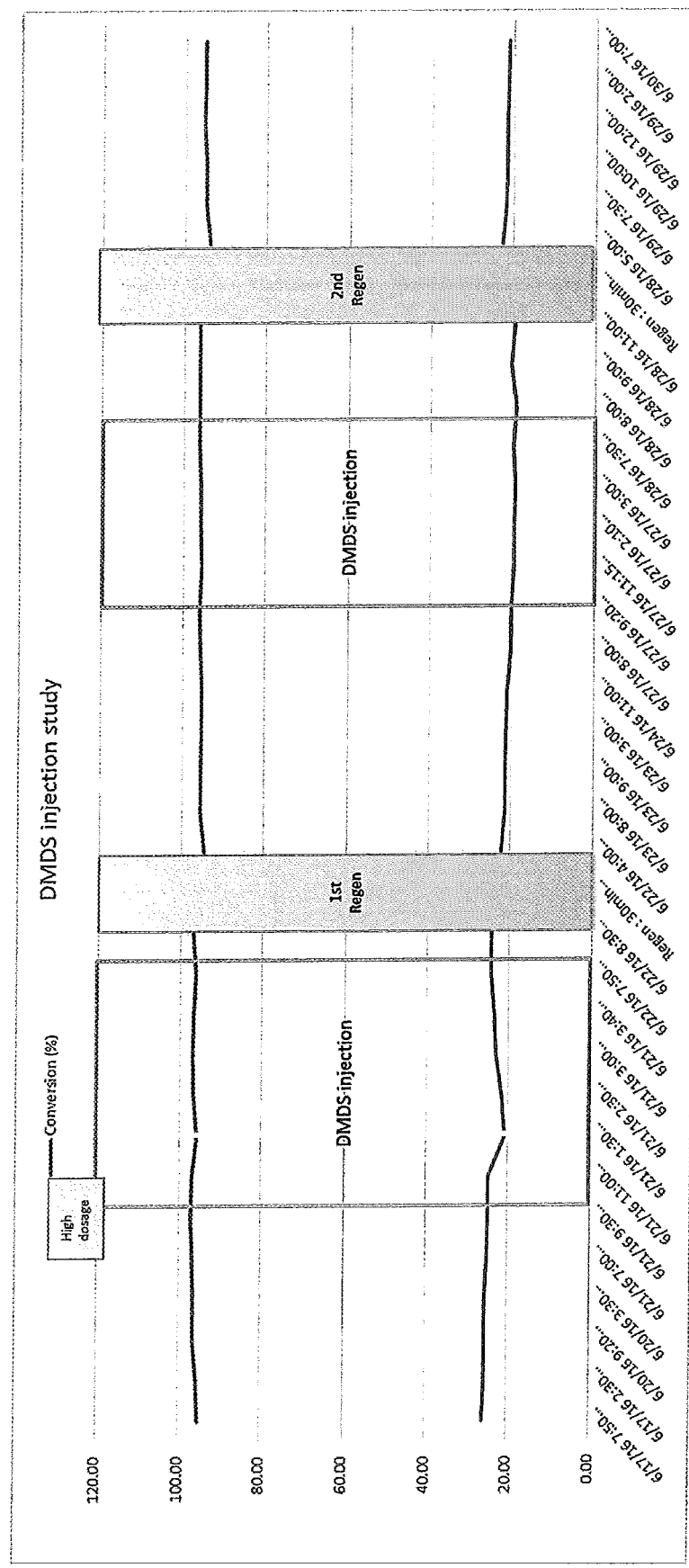
FIG. 4 is a long term microreactor unit (MRU) run with dimethyl disulfide DMDS injections.

Results are shown in FIG. 4, the ODH catalyst activity and selectivity dropped only with very high dosage (0.22 ml of DMDS injection in 10 mins, corresponding to 19.38 wt.-% of DMDS in the feed), which was simulating the conditions of extreme carryover of DMDS to reactor, which would be possible in case of DMDS injection process upset. For normal injection rate (0.21 ml/16 hours, corresponding to 0.2249 wt.-% of DMDS in the feed), the impact on activity and selectivity was not noticeable.

TABLE 1

Short term MRU run at 365° C. with 3000 space velocity (h−1)

|  | Time | Conversion (%) | Selectivity (%) |
|---|---|---|---|
| Before DMDS injection | Nov 23, 2016 | 25.95 | 89.24 |
| During DMDS injection, 0.2 ml over 5 h, corresponding to 0.7162 wt.-% of DMDS in the feed | Nov 23, 2016, 11:36 AM | 24.76 | 89.06 |
|  | Nov 23, 2016, 1:20 PM | 24.57 | 89.22 |
|  | Nov 23, 2016, 2:30 PM | 24.42 | 89.31 |
| after DMDS injection | Nov 23, 2016, 3:13 PM | 24.29 | 89.28 |
|  | Nov 23, 2016, 3:30 pm | 24.36 | 89.40 |

Another short term run test was conducted with a different batch of ODH catalyst and as shown in Table 1, the activity and selectivity was not changed due to (DMDS) injection (0.2 ml/5 hr).

Various Embodiments

1. A chemical complex for oxidative dehydrogenation of lower alkanes, the chemical complex comprising in cooperative arrangement:
   i) at least two mixers for premixing an oxygen containing gas and a lower alkane containing gas to produce a mixed feedstock stream and additionally comprising a cleaning loop; and
   ii) at least one oxidative dehydrogenation reactor;
   wherein the at least two mixers are connected in parallel to the at least one oxidative dehydrogenation reactor so that either a first gas mixing unit or a second gas mixing unit is connected to the at least one oxidative dehydrogenation reactor during normal operations; and
   wherein an oxidative dehydrogenation catalyst contained within the at least one oxidative dehydrogenation reactor reacts with the mixed feed stock stream to produce a product stream comprising the corresponding alkene.

2. The chemical complex of embodiment 1, wherein the cleaning loop comprises a pump, a filter and a small heating vessel.

3. The chemical complex of any of the previous embodiments, further comprising a knock-out vessel, after the mixed feedstock stream outlet and in close proximity to the at least one oxidative dehydrogenation reactor, wherein the knock-out vessel is configured to receive a condensed cleaning solvent.

4. The chemical complex of any of the previous embodiments, further comprising a feedline connecting each of the at least two mixers to the at least one oxidative dehydrogenation reactor, wherein the feedlines are fitted with sprayers to introduce a cleaning solvent to internal walls of the feedline.

5. The chemical complex of any of the previous embodiments wherein each of the at least two mixers are flooded gas mixers.

6. The chemical complex of any of the previous embodiments wherein each of the at least two flooded gas mixers comprises:
   a. a closed mixing vessel having a top end, a bottom end, and flooded with a non-flammable liquid;

b. a liquid supply nozzle for introducing a cleaning solvent into the closed mixing vessel in close proximity to the top end;

c. a liquid supply nozzle for introducing a non-flammable liquid into the closed mixing vessel in close proximity to the top end;

d. a drain connection for removing non-flammable liquid from the closed mixing vessel located in close proximity to the lowest point of the bottom end;

e. at least one lower alkane containing gas supply nozzle for introducing lower alkane containing gas into the closed mixing vessel near the bottom end;

f. at least one oxygen containing gas supply nozzle for introducing oxygen containing gas into the closed mixing vessel near the bottom end;

g. at least one means within the closed mixing vessel for internal mixing of introduced lower alkane containing gas with oxygen containing gas to form the mixed feedstock stream; and h. a mixed feedstock stream outlet located in close proximity to the uppermost point of the top end;

wherein the level of non-flammable liquid within the closed mixing vessel is at a height sufficient to allow mixing of the introduced lower alkane containing gas and the oxygen containing gas before reaching the top end such that bubbles of gas exiting the non-flammable liquid comprise a mixture of lower alkane containing gas and oxygen containing gas that is outside the flammability limit.

7. The complex of any of the previous embodiments wherein the non-flammable liquid is water.

8. The complex of any of the previous embodiments wherein the means for internal mixing is chosen from: a. a static mixer; b. a packed bed; c. a structured bed; and d. an impeller.

9. The complex of any of the previous embodiments, further comprising:
   i) a quench tower for quenching the product stream and for removing water and soluble oxygenates from the product stream;
   ii) an amine wash for removing carbon dioxide from the product stream;
   iii) a dryer for removal of water from the product stream;
   iv) a distillation tower for removing C2/C2+ hydrocarbons from the product stream to produce an overhead stream enriched with C1 hydrocarbons;
   v) optionally, a means for introducing a combustible fuel into the overhead stream; and
   vi) an oxygen separation module;
   wherein the components in i) through vi) are connected in series in the sequence described, the overhead stream from iv) may be directed into the retentate side, said permeate side, or both the retentate side and the permeate side, and the oxygen enriched gas and combustion products from the permeate side may be directed back to ii) as or part of the oxygen containing gas introduced into the at least one oxidative dehydrogenation reactor.

10. The chemical complex of any of the previous embodiments wherein the oxidative dehydrogenation catalyst comprises a mixed metal oxide chosen from:
    i) catalysts of the formula:

$Mo_aV_bTe_cNb_dPd_eO_f$ wherein a, b, c, d, e and f are the relative atomic amounts of the elements Mo, V, Te, Nb, Pd and O, respectively; and when a=1, b=0.01 to 1.0, c=0.01 to 1.0, d=0.01 to 1.0, 0.00≤e≤0.10 and f is a number to satisfy the valence state of the catalyst;

ii) catalysts of the formula:

$Ni_gA_hB_iD_jO_f$ wherein: g is a number from 0.1 to 0.9, for example from 0.3 to 0.9, or for example from 0.5 to 0.85, or for example 0.6 to 0.8; h is a number from 0.04 to 0.9; i is a number from 0 to 0.5; j is a number from 0 to 0.5; and f is a number to satisfy the valence state of the catalyst; A is chosen from Ti, Ta, V, Nb, Hf, W, Y, Zn, Zr, Si and Al or mixtures thereof; B is chosen from La, Ce, Pr, Nd, Sm, Sb, Sn, Bi, Pb, Tl, In, Te, Cr, Mn, Mo, Fe, Co, Cu, Ru, Rh, Pd, Pt, Ag, Cd, Os, Ir, Au, Hg, and mixtures thereof; D is chosen from Ca, K, Mg, Li, Na, Sr, Ba, Cs, and Rb and mixtures thereof; and O is oxygen;

iii) catalysts of the formula:

$Mo_aE_kG_lO_f$ wherein: E is chosen from Ba, Ca, Cr, Mn, Nb, Ta, Ti, Te, V, W and mixtures thereof; G is chosen from Bi, Ce, Co, Cu, Fe, K, Mg, V, Ni, P, Pb, Sb, Si, Sn, Ti, U, and mixtures thereof; a=1; k is 0 to 2; l=0 to 2, with the proviso that the total value of l for Co, Ni, Fe and mixtures thereof is less than 0.5; and f is a number to satisfy the valence state of the catalyst;

iv) catalysts of the formula:

$V_mMo_nNb_oTe_pMe_qO_f$ wherein: Me is a metal chosen from Ta, Ti, W, Hf, Zr, Sb and mixtures thereof; m is from 0.1 to 3; n is from 0.5 to 1.5; o is from 0.001 to 3; p is from 0.001 to 5; q is from 0 to 2; and f is a number to satisfy the valence state of the catalyst; and v) catalysts of the formula:

$Mo_aV_rX_sY_tZ_uM_vO_f$ wherein: X is at least one of Nb and Ta; Y is at least one of Sb and Ni; Z is at least one of Te, Ga, Pd, W, Bi and Al; M is at least one of Fe, Co, Cu, Cr, Ti, Ce, Zr, Mn, Pb, Mg, Sn, Pt, Si, La, K, Ag and In; a=1.0 (normalized); r=0.05 to 1.0; s=0.001 to 1.0; t=0.001 to 1.0; u=0.001 to 0.5; v=0.001 to 0.3; and f is a number to satisfy the valence state of the catalyst.

11. The chemical complex of any of the previous embodiments wherein the at least one oxidative dehydrogenation reactor is chosen from a single fixed bed type reactor, tube in shell heat exchanger fixed bed type reactor, a single fluidized bed type reactor, and a swing bed type reactor arrangement.

12. The chemical complex of any of the previous embodiments wherein the at least one oxidative dehydrogenation reactor comprises more than one oxidative dehydrogenation reactor connected in parallel and each comprising the same or different oxidative dehydrogenation catalyst.

13. The chemical complex of any of the previous embodiments wherein C2/C2+ hydrocarbons leave the distillation tower and are directed to a splitter for separation of unreacted lower alkane and corresponding alkene into an unreacted lower alkane stream and a corresponding alkene stream.

14. A process for removing sulfur-containing deposits during the operation of an oxidative dehydrogenation reactor complex, the process comprising:
    i) operating a chemical complex comprising in cooperative arrangement:
        a. at least two mixers for premixing an oxygen containing gas and a lower alkane containing gas to produce a mixed feedstock stream; and
        b. at least one oxidative dehydrogenation reactor,
    wherein the at least two mixers are connected in parallel to the at least one oxidative dehydrogenation reactor so that either a first gas mixing unit or a second gas mixing unit is connected to the at least one oxidative dehydrogenation reactor during normal operations; and wherein an oxidative dehydrogenation catalyst contained within the at least one oxidative dehydrogenation reactor reacts with the mixed feed stock stream to produce a product stream comprising the corresponding alkene;
- ii) monitoring the pressure within the chemical complex during normal operation;
- iii) switching from a first mixer for premixing the oxygen containing gas and the lower alkane containing gas to a second mixer when a pressure drop is observed;
- iv) introducing a cleaning solvent into the first mixer and cycling the cleaning solvent through a cleaning loop until the sulfur-containing deposits are removed;
- v) continuing to monitor the pressure within the complex during normal operation;
- vi) switching back to the first mixer when a pressure drop is observed;
- vii) introducing the cleaning solvent into the second mixer and cycling a cleaning solvent through a cleaning loop until the sulfur-containing deposits are removed; and
- viii) repeating steps i)-vii) during continued operation of the chemical complex.

15. The process of any of the previous embodiments wherein the cleaning loop comprises a pump a filter and a small heating vessel.

16. The process of any of the previous embodiments wherein the cleaning loop comprises a pump a filter and a small heating vessel.

17. The process of any of the previous embodiments wherein the cleaning loop comprises a pump a filter and a small heating vessel and the cleaning solvent is warmed to between about 60° C. and about 80° C. in the heating vessel.

18. The process of any of the previous embodiments wherein prior to introducing the cleaning solvent in steps vi) and vii) the first or second mixer is drained, then flushed and dried with an inert gas.

19. The process of any of the previous embodiments wherein the cleaning solvent is DMDS.

20. The process of any of the previous embodiments wherein the cleaning solvent further comprises an additional component.

21 The process of any of the previous embodiments wherein the additional component in the cleaning solvent is sodium bisulfate.

22 The process of any of the previous embodiments wherein the cleaning solvent is DMDS and sodium bisulfate.

23. The process of any of the previous embodiments wherein the chemical complex further comprises a knock-out vessel in-line with and in close proximity to the at least one oxidative dehydrogenation reactor wherein the knock-out vessel is configured to receive condensed cleaning solvent and reduce the amount of liquid cleaning solvent that enters the at least one oxidative dehydrogenation reactor.

24. A process for removing sulfur-containing deposits during the operation of an oxidative dehydrogenation reactor complex, the process comprising:
- i) operating a chemical complex comprising in cooperative arrangement:
  - a. at least two mixers for premixing an oxygen containing gas and a lower alkane containing gas to produce a mixed feedstock stream;
  - b. at least one oxidative dehydrogenation reactor, and
  - c. a feedline connecting each of the at least two mixers to the at least one oxidative dehydrogenation reactor, wherein the feedlines are fitted with sprayers to introduce a cleaning solvent to internal walls of the feedline.

wherein the at least two mixers are connected by the feedline in parallel to the at least one oxidative dehydrogenation reactor so that either a first gas mixing unit or a second gas mixing unit is connected to the at least one oxidative dehydrogenation reactor during normal operations; and wherein an oxidative dehydrogenation catalyst contained within the at least one oxidative dehydrogenation reactor reacts with the mixed feed stock stream to produce a product stream comprising the corresponding alkene;
- ii) monitoring the pressure within the chemical complex during normal operation;
- iii) introducing the cleaning solvent into the feedline through the sprayer to remove sulfur containing deposits when a pressure drop is observed in the chemical complex;
- iv) continuing to monitor the pressure within the chemical complex during operations and while the cleaning solvent is being introduced;
- v) stop the cleaning solvent flow once the pressure in the chemical complex returns to normal operating levels.

We claim:

1. A chemical complex for the oxidative dehydrogenation of lower alkanes, the chemical complex comprising in cooperative arrangement:
- i) at least two mixers for premixing an oxygen containing gas and a lower alkane containing gas to produce a mixed feedstock stream and additionally comprising a cleaning loop; and
- ii) at least one oxidative dehydrogenation reactor;

wherein the at least two mixers are connected in parallel to the at least one oxidative dehydrogenation reactor so that either a first gas mixing unit or a second gas mixing unit is connected to the at least one oxidative dehydrogenation reactor during normal operations; and wherein an oxidative dehydrogenation catalyst contained within the at least one oxidative dehydrogenation reactor reacts with the mixed feed stock stream to produce a product stream comprising the corresponding alkene.

2. The chemical complex of claim 1, wherein the cleaning loop comprises a pump, a filter, and a small heating vessel.

3. The chemical complex of claim 1, further comprising a knock-out vessel, after the mixed feedstock stream outlet and in close proximity to the at least one oxidative dehydrogenation reactor, wherein the knock-out vessel is configured to receive a condensed cleaning solvent.

4. The chemical complex of claim 1, further comprising a feedline connecting each of the at least two mixers to the at least one oxidative dehydrogenation reactor, wherein the feedlines are fitted with sprayers to introduce a cleaning solvent to internal walls of the feedline.

5. The chemical complex of claim 1, wherein each of the at least two mixers are flooded gas mixers.

6. The chemical complex of claim 5, wherein each of the at least two flooded gas mixers comprise:
- a. a closed mixing vessel having a top end, a bottom end, and flooded with a non-flammable liquid;
- b. a liquid supply nozzle for introducing a cleaning solvent into the closed mixing vessel in close proximity to the top end;
- c. a liquid supply nozzle for introducing a non-flammable liquid into the closed mixing vessel in close proximity to the top end;

d. a drain connection for removing non-flammable liquid from the closed mixing vessel located in close proximity to the lowest point of the bottom end;
e. at least one lower alkane containing gas supply nozzle for introducing a lower alkane containing gas into the closed mixing vessel near the bottom end;
f. at least one oxygen containing gas supply nozzle for introducing an oxygen containing gas into the closed mixing vessel near the bottom end;
g. at least one means within the closed mixing vessel for internal mixing of the introduced lower alkane containing gas with the oxygen containing gas to form the mixed feedstock stream; and
h. a mixed feedstock stream outlet located in close proximity to the uppermost point of the top end;
wherein the level of the non-flammable liquid within the closed mixing vessel is at a height sufficient to allow mixing of the introduced lower alkane containing gas and the oxygen containing gas before reaching the top end such that bubbles of gas exiting the non-flammable liquid comprise a mixture of the lower alkane containing gas and the oxygen containing gas that is outside the flammability limit.

7. The chemical complex of claim 6 wherein the non-flammable liquid is water.

8. The chemical complex of claim 6 wherein the means for internal mixing is chosen from:
   a. a static mixer;
   b. a packed bed;
   c. a structured bed; and
   d. an impeller.

9. The chemical complex of claim 1, further comprising:
i) a quench tower for quenching the product stream and for removing water and soluble oxygenates from the product stream;
ii) an amine wash for removing carbon dioxide from the product stream;
iii) a dryer for removal of water from the product stream;
iv) a distillation tower for removing C2/C2+ hydrocarbons from the product stream to produce an overhead stream enriched with C1 hydrocarbons;
v) optionally, a means for introducing a combustible fuel into the overhead stream; and
vi) an oxygen separation module;
wherein the components in i) through vi) are connected in series in the sequence described, the overhead stream from iv) may be directed into the retentate side, the permeate side, or both the retentate side and the permeate side, and the oxygen enriched gas and combustion products from the permeate side may be directed back to ii) as or part of the oxygen containing gas introduced into the at least one oxidative dehydrogenation reactor.

10. The chemical complex of claim 9, wherein the oxidative dehydrogenation catalyst comprises a mixed metal oxide chosen from:
i) a catalyst of the formula:

$$Mo_aV_bTe_cNb_dPd_eO_f$$

wherein a, b, c, d, e and f are the relative atomic amounts of the elements Mo, V, Te, Nb, Pd, and O, respectively; and when a=1, b=0.01 to 1.0, c=0.01 to 1.0, d=0.01 to 1.0, 0.00≤e≤0.10 and f is a number to satisfy the valence state of the catalyst;
ii) a catalyst of the formula:

$$Ni_gA_hB_iD_jO_f$$

wherein: g is a number from 0.1 to 0.9; h is a number from 0.04 to 0.9; i is a number from 0 to 0.5; j is a number from 0 to 0.5; and f is a number to satisfy the valence state of the catalyst; A is chosen from Ti, Ta, V, Nb, Hf, W, Y, Zn, Zr, Si, and Al or mixtures thereof; B is chosen from La, Ce, Pr, Nd, Sm, Sb, Sn, Bi, Pb, Tl, In, Te, Cr, Mn, Mo, Fe, Co, Cu, Ru, Rh, Pd, Pt, Ag, Cd, Os, Ir, Au, Hg, and mixtures thereof; D is chosen from Ca, K, Mg, Li, Na, Sr, Ba, Cs, Rb, and mixtures thereof; and O is oxygen;
iii) a catalyst of the formula:

$$Mo_aE_kG_lO_f$$

wherein: E is chosen from Ba, Ca, Cr, Mn, Nb, Ta, Ti, Te, V, W, and mixtures thereof; G is chosen from Bi, Ce, Co, Cu, Fe, K, Mg, V, Ni, P, Pb, Sb, Si, Sn, Ti, U, and mixtures thereof; a=1; k is 0 to 2; l=0 to 2, with the proviso that the total value of l for Co, Ni, Fe, and mixtures thereof is less than 0.5; and f is a number to satisfy the valence state of the catalyst;
iv) a catalyst of the formula:

$$V_mMo_nNb_oTe_pMe_qO_f$$

wherein: Me is a metal chosen from Ta, Ti, W, Hf, Zr, Sb, and mixtures thereof; m is from 0.1 to 3; n is from 0.5 to 1.5; o is from 0.001 to 3; p is from 0.001 to 5; q is from 0 to 2; and f is a number to satisfy the valence state of the catalyst; and
v) a catalyst of the formula:

$$Mo_aV_rX_sY_tZ_uM_vO_f$$

wherein: X is at least one of Nb and Ta; Y is at least one of Sb and Ni; Z is at least one of Te, Ga, Pd, W, Bi, and Al; M is at least one of Fe, Co, Cu, Cr, Ti, Ce, Zr, Mn, Pb, Mg, Sn, Pt, Si, La, K, Ag, and In; a=1.0 (normalized); r=0.05 to 1.0; s=0.001 to 1.0; t=0.001 to 1.0; u=0.001 to 0.5; v=0.001 to 0.3; and f is a number to satisfy the valence state of the catalyst.

11. The chemical complex of claim 9, wherein the at least one oxidative dehydrogenation reactor is chosen from a single fixed bed type reactor, tube in shell heat exchanger fixed bed type reactor, a single fluidized bed type reactor, and a swing bed type reactor arrangement.

12. The chemical complex of claim 9, wherein the at least one oxidative dehydrogenation reactor comprises more than one oxidative dehydrogenation reactor connected in parallel and each comprising the same or different oxidative dehydrogenation catalyst.

13. The chemical complex of claim 9, wherein C2/C2+ hydrocarbons leave the distillation tower and are directed to a splitter for separation of unreacted lower alkane and corresponding alkene into an unreacted lower alkane stream and a corresponding alkene stream.

* * * * *

UNITED STATES PATENT AND TRADEMARK OFFICE
CERTIFICATE OF CORRECTION

PATENT NO. : 11,111,194 B2
APPLICATION NO. : 16/249992
DATED : September 7, 2021
INVENTOR(S) : Vasily Simanzhenkov et al.

It is certified that error appears in the above-identified patent and that said Letters Patent is hereby corrected as shown below:

On the Title Page

Item (72), Inventors, please correct inventor's name from "Christina Orta" to -- Cristina Orta --

Signed and Sealed this
Nineteenth Day of October, 2021

Drew Hirshfeld
*Performing the Functions and Duties of the*
*Under Secretary of Commerce for Intellectual Property and*
*Director of the United States Patent and Trademark Office*